(12) United States Patent
Periana et al.

(10) Patent No.: US 7,915,459 B2
(45) Date of Patent: Mar. 29, 2011

(54) CATALYTIC SYSTEMS FOR THE CONVERSION OF HYDROCARBONS TO FUNCTIONALIZED PRODUCTS

(76) Inventors: Roy A. Periana, Marina Del Rey, CA (US); William A. Goddard, III, Pasadena, CA (US)

( * ) Notice: Subject to any disclaimer, the term of this patent is extended or adjusted under 35 U.S.C. 154(b) by 1122 days.

(21) Appl. No.: 11/361,315

(22) Filed: Feb. 24, 2006

(65) Prior Publication Data

US 2006/0241327 A1    Oct. 26, 2006

Related U.S. Application Data

(60) Provisional application No. 60/656,556, filed on Feb. 24, 2005, provisional application No. 60/656,264, filed on Feb. 24, 2005.

(51) Int. Cl.
*C07C 29/48* (2006.01)
(52) U.S. Cl. .................................. 568/910; 568/910.5
(58) Field of Classification Search .................. 568/910, 568/910.5
See application file for complete search history.

(56) References Cited

U.S. PATENT DOCUMENTS

| 2,437,648 | A | 3/1948 | Milas et al. |
| 5,233,113 | A | 8/1993 | Periana et al. |
| 5,306,855 | A | 4/1994 | Periana et al. |
| 5,723,697 | A | 3/1998 | Bhinde et al. |
| 6,685,772 | B2 | 2/2004 | Goddard et al. |
| 6,777,510 | B1 | 8/2004 | Philipp et al. |
| 2004/0055299 | A1 | 3/2004 | Bernard |

FOREIGN PATENT DOCUMENTS

| DE | 501467 | 7/1930 |
| EP | 0 531 715 | 3/1993 |
| EP | 1 350 783 | 10/2003 |
| JP | 09 087215 A | 3/1997 |
| WO | 2005/120198 | 12/2005 |

OTHER PUBLICATIONS

Goldstein al., "Hydroxylation of Methane by a Sterically Hindered Ruthenium Complex", *J. Chem. Soc., Chem. Commun.* 21-22 (1991).
Lin et al., "Catalytic Carbon-Carbon and Carbon-Hydrogen Bond Cleavage in Lower Alkanes. Low-Temperature Hydroxylations and Hydroxycarbonylations with Dioxygen as the Oxidant", *J. Am. Chem. Soc.* 118(19):4574-4580 (1996).
Shul 'Pin et al., "Oxygenation of alkanes with hydrogen peroxide catalysed by osmium complexes", *Chem. Commun.* 1131-1132 (2000).
Wang et al., "Oxidative carbonylation of methane to methyl acetate on rhodium-doped iron phosphate catalyst", *Chem. Commun.* 1187-1188 (1997).
Kitamura et al., "Photo-splitting of Water to Dihydrogen and Hydroxyl Radicals Catalysed by Rhodium-deposited Perfluorinated Poly(p-phyenylene)", *J. Chem. Soc., Chem. Commun.* 2189-2190 (1995).
Tenn et al. "CH Activation with an O-Donor Iridium-Methoxo Complex" *J. Am. Chem. Soc.* 2005, 127, 14172-14173.
Bhalla et al. "Synthesis, Structure, and Reactivity of O-Donor Ir(III) Complexes: C-H Activation Studies with Benzene" *J. Am. Chem. Soc.* 2005, 127, 11372-11389.
Liu et al. "Synthesis and Structural Characterization of Novel Organometallic, Rh(III), Bis(acetylacetonate) Complexes" *Organometallics* 2004, 23, 3584-3586.
Wong-Foy et al. "Alkane C-H Activation and Catalysis by an O-Donor Ligated Iridium Complex" *J. Am. Chem. Soc.* 2003, 125, 14292-14293.
Krogh-Jespersen et al. "Combined Computational and Experimental Study of Substituent Effects on the Thermodynamics of H2, CO, Arene, and Alkane Addition to Iridium" *J. Am. Chem. Soc.* 2002, 124, 10797-10809.
Espenson, J. "Atom-transfer reactions catalyzed by methyltrioxorhenium(VII)—mechanisms and applications" *Chem. Commun.* 1999, 479-488.
Brown et al. "Phenyl-to-Oxo Migration in an Electrophillic Rhenium(VII) Dioxo Complex" *J. Am. Chem. Soc.* 1996, 118, 12119-12133.
Abu-Omar et al. "Deactivation of Methylrhenium Trioxide-Peroxide Catalysis by Diverse and Competing Pathways" *J. Am. Chem. Soc.* 1996, 118, 4966-4974.

*Primary Examiner* — Elvis O Price
(74) *Attorney, Agent, or Firm* — Pillsbury Winthrop Shaw Pittman LLP

(57) ABSTRACT

This invention discloses methods and processes for selectively converting hydrocarbons such as methane to materials such as alcohols or other materials containing more reactive functionalities.

19 Claims, 30 Drawing Sheets

$$CH_4 + SeO_4^{2-} \xrightarrow{H_2O/OH^-/Cat} CH_3OH + SeO_3^{2-}$$
$$\Delta G = -16 \text{ kcal/mol}$$
$$SeO_3^{2-} + \tfrac{1}{2} O_2 \text{ (air)} \rightarrow SeO_4^{2-} \quad \Delta G = -16 \text{ kcal/mol}$$

$$\text{Net: } CH_4 + \tfrac{1}{2} O_2 \rightarrow CH_3OH$$

FIG 18

Destabilization
O-p-π to M-d-π repulsion

Stabilization
O-p-π to M-d-π Back-Bonding

CATALYTIC SYSTEMS FOR THE CONVERSION OF HYDROCARBONS TO FUNCTIONALIZED PRODUCTS

This application claims benefit of U.S. Provisional Application No. 60/656,264, filed Feb. 24, 2005, and U.S. Provisional Application No. 60/656,556, filed Feb. 24, 2005.

BACKGROUND OF THE INVENTION

Raw hydrocarbons are currently converted to commercially more useful materials by multi-step and/or high temperature processes, typically above 300° C. This leads to expensive reactors, extensive heat management and subsequent high capital and operating costs. In conversions developed to date, the key chemical challenge is the direct, selective conversion of C—H or CC bonds of hydrocarbons at lower temperatures to produce functional bonds such as C—OH, C=C, other C—C or other C—X bonds where X is a heteroatom. In general, present oxidation catalyst technology for C—H and CC conversion is not sufficiently selective to allow direct conversion processes due to the involvement of radical and especially free radical reaction pathways, for example Bhinde et al. (U.S. Pat. No. 5,723,697) incorporated herein by reference in its entirety. There is thus a need for new catalysts for converting the C—H bond to functionalized bonds that can be utilized for the conversion of hydrocarbons to more useful materials under milder and more selective conditions.

Efficient catalytic systems for the low temperature, selective oxidation of hydrocarbon alkanes to alcohols, X=OH, are Pt(II) and Hg(II) all operate in strongly acidic media. See for example Periana et al. (U.S. Pat. No. 5,233,113, U.S. Pat. No. 5,306,855 and US Patent Application 2003/0120125) incorporated herein by reference in their entirety. The metals Pt and Hg have been reported to catalyze the conversion of methane in concentrated sulfuric acid to methyl esters with formation of reduced oxidant. Subsequent hydrolysis of the methyl ester and reoxidation of the reduced oxidant comprised a complete system for the selective oxidation of methane to methanol.

A problem in devising a catalytic process for the partial oxidation of alkanes is the non-reactive nature of the alkane C—H bond and the difficulty in finding a catalytic substance which will promote activation of, and subsequent reaction at, one or more of the C—H bonds of the alkane reactant without also catalyzing complete oxidation of the alkane in question—e.g., methane to $CO_2$. This threshold problem has been solved, to at least some degree, by the catalytic process described in U.S. Pat. Nos. 5,233,113, 5,306,855 and US Patent Application 2003/0120125).

A major disadvantage of the Pt(II) or Hg(II) systems in strong acid is that only ~1M methanol could be developed before the reaction effectively stopped due to the effective drop in solvent acidity. This product inhibition leads to impractically high separation costs. The primary reason for this limitation in product concentration is that as both the methanol and water build up in the reaction product mixture, these molecules preferentially coordinate to the Hg(II) ions and inhibit catalysis. Consequently, designing catalysts that are not inhibited by water or product is one of the central challenges to developing catalysts that efficiently oxidize alkanes to alcohols.

SUMMARY OF THE INVENTION

This invention discloses the design of new catalysts that facilitates the conversion of C—H bonds of hydrocarbons to functionalized bonds such as C—O, C=C, C—C and C—X, where X is a heteroatom. Specifically, this invention pertains to the use of basic solvents, such as solutions of amines containing the conjugate base amides, solutions of alcohols containing the conjugate base alkoxides, water containing hydroxides, molten salt mixtures of bases such as NaOH/KOH or $NaNH_2/KNH_2$ as a reaction solutions into which are dissolved metal ions (or other catalyst) and oxidants that can be used for the direct, selective, facile conversion of hydrocarbons to more useful products.

Many metals of the periodic table can be considered for this invention. Suitable metal ions include but are not limited to electropositive transition metals such as Re, Os, Ir, Ru, W, and Rh in intermediate oxidation states, for example Re(I), Os(II), Ir(I), Ru(II). Other metals may be suitable when as well, including Pt(II) as well as other metal ions that produce basic metal hydroxides in aqueous media.

One aspect of the present invention is a method for activating a hydrocarbon in non-acidic media which comprises contacting a C—H bond of the hydrocarbon with a solvent-assisted, non-radical producing catalyst.

Another aspect of this invention is the use of basic solvents, rather than neutral or inert organic solvents such as toluene, $CH_2Cl_2$, benzene, cyclohexane, THF and the like that have been used with the transition metal catalysts by many practitioners in the field. In basic solvents, it is expected that the active catalysts will:

a) facilitate activation of hydrocarbons like alkane and arenes by allowing facile generation of open coordination sites on the metal catalyst that allow coordination between the hydrocarbon and the metal catalyst
b) keep the metal catalyst soluble;
c) prevent deactivation of the metal catalyst by water or oxidation products;
d) prevent or minimize reaction with the desired product (protection of the product) and
e) allow the use of dioxygen molecule ($O_2$) as the terminal oxidant.

The use of basic solvents along with the use of lower oxidation state ions such as Os(II), Re(I), Ir(III), increases the reactivity of these low oxidation state, $d^6$ metal ions One embodiment of the present invention are methods for activating a hydrocarbon in non-acidic media which comprises contacting a C—H bond of the hydrocarbon with a solvent-assisted catalyst that does not operate by the generation of free radicals.

Another embodiment of the present invention is a method for activating a hydrocarbon in non-acidic media which comprises contacting a C—H bond of the hydrocarbon with a solvent-assisted catalyst that does not operate by the generation of free radicals. In one aspect, the catalyst comprises a transition metal ion and at least one ligand. Non limiting examples of transition metals include Ir, Os, Re, W, Rh and Ru. Non-limiting examples of ligands include those which comprise one, two, three or four ligating atoms selected from periodic Group IV, V, and VI, or combinations thereof. Non-limiting examples of oxygen containing ligands include hydroxy, alkoxy, oxo, carboxylate, optionally substituted diol, optionally substituted polyol, and optionally substituted acetylacetonate. Other non-limiting examples include ligands that chelate having at least two ligating atoms O atom termini linked via a conjugated π-system such as, but not limited to an optionally substituted acetylacetonate. Other examples include tropolone, aryloxide, catechol, hydroxyacetophenone.

Non-limiting examples of nitrogen containing ligands include ammine, optionally substituted amine, optionally substituted amide, optionally substituted nitrogen heterocycle, optionally substituted chelating diamine, optionally substituted chelating polyamine, optionally substituted chelating amide, and optionally substituted linked nitrogen heterocycle. Non limiting examples of linked nitrogen heterocycles include optionally substituted bipyridine, optionally substituted bipyrazine, and optionally substituted bipyrimidine.

According to another embodiment of the invention, the basic media is a solvent. Non-limiting examples include neutral solvents and basic solvents. Other non-limiting examples include amine containing the conjugate base amides, alcohols containing the conjugate base alkoxides, water-containing hydroxides, molten salt mixtures such as NaOH/KOH or $NaNH_2/KNH_2$. According to another embodiment, the non acid media is a solid support. Another aspect of the invention is that hydrocarbon activation is accelerated by solvent. Non limiting examples of such solvents include basic and highly basic solvents.

Suitable non-limiting examples of hydrocarbons which may be selectively activated according to methods disclosed herein include alkanes and arenes, for example methane and benzene.

Another embodiment of the present invention is that hydrocarbon activated by methods disclosed herein result in formation of a metal-alkyl complexes which may be further transformed to useful products. Accordingly, the present invention embodies a process for selectively oxidizing hydrocarbons including the following steps:
(1) activating a hydrocarbon C—H bond by contact with a solvent-assisted, non-radical, producing catalyst in non acidic media;
(2) transforming an activated hydrocarbon, via an oxygen insertion agent, to a functionalized hydrocarbon and a reduced oxidant; and
(3) releasing an oxidized hydrocarbon.
Suitable non-limiting examples of hydrocarbons which may be selectively or partially oxidized according to methods disclosed herein include alkanes and arenes, for example methane and benzene.

A non-limiting example of step (1) is a process wherein the hydrocarbon activation results in formation of a metal-alkyl covalent bond. A non-limiting example of step (2) is a process wherein a metal alkyl is converted to a metal alkoxides via oxygen insertion agent. Non-limiting examples of a O-atom donors include amine-N-oxide, cupric oxide, iron oxide, periodate, vanadate, nitrous oxide, hydrogen peroxide, sellenate ($SeO_4^{2-}$), hypochlorite ($ClO^-$), chlorite ($ClO_2^-$,), nitrate ($NO_3^-$), molybdates, tellurates, and sulfur oxides.

According to one aspect of the invention, reduced oxidants may be regenerated in separated reactors to regenerate an oxygen insertion agents. A non-limiting example of such a reduced oxidant is $SeO_3^{2-}$, which is recycled back to $SeO_4^{2-}$ in a separate reactor using air or oxygen as a reoxidizing agent.

According to another embodiment, the processes may be combined into a catalytic cycle for partially oxidizing C—H bonds. A non-limiting example of such a process is one which comprises the following steps:
(1) passing a feed comprising hydrocarbon and an oxidant to a first catalyst zone comprising a soluble catalyst and an oxidation stable solvent, at functionalization conditions, to form an effluent comprising oxygenated hydrocarbon and reduced oxidant;
(2) separating the oxygenated hydrocarbon from the reduced oxidant;
(3) passing the reduced oxidant and an reoxidizer to an oxidation zone, at reoxidizing conditions, to reform the oxidant; wherein the catalyst comprises one or more metals selected from the group consisting of Re, Os, Ir, Ru, W, and Rh, where the metal is coordinated to one or more oxidation resistant ligands, and wherein the functionalization conditions comprise a temperature of between 100 and 350 degrees C. and an acidity level selected from the group consisting of neutral, basic, highly basic and super basic.

According to another embodiment, step (1) of the process may be carried out using catalysts supported on solid supports.

Suitable feed hydrocarbons include but are not limited to alkanes and arenes, which yield, alkanols and phenols respectively. oxygenated hydrocarbon is methanol. Suitable temperatures are between 150 and 250 degrees C.

According to one embodiment of the process, the reoxidizer is oxygen. According to another embodiment of the process, the reoxidizer is air.

Another embodiment of the present invention are methods of identifying a hydrocarbon C—H bond activation catalyst comprising the steps
determining a pH value for a metal aquo complex in aqueous solution and selecting metal catalysts which increase solution pH;
determining the change in Gibbs free energy for forming a metal alkyl complex from a corresponding metal hydroxy complex and selecting catalysts with values below a threshold value.

According to the present invention, pH values and Gibbs free energy values may be experimentally or computationally determined.

Another embodiment of the present invention are method of identifying a hydrocarbon C—H bond activation catalyst which operates in non acidic media comprising the steps
contacting a candidate catalyst with a hydrocarbon in a deuterated solvent under activating conditions;
detecting deuterium incorporation in the hydrocarbon.

Other objects and advantages of the present invention will be apparent upon reading the following non-restrictive description of several preferred embodiments, made with reference to the accompanying drawings.

BRIEF DESCRIPTION OF THE DRAWINGS

FIG. 13 shows a catalytic cycle for the conversion of hydrocarbons to alcohols based on the M-OH reaction.

FIG. 18 shows the net oxidation and favorable thermodynamics for the oxidation of methane with an air of oxygen recyclable oxidant.

DETAILED DESCRIPTION OF THE INVENTION

Figure 1:
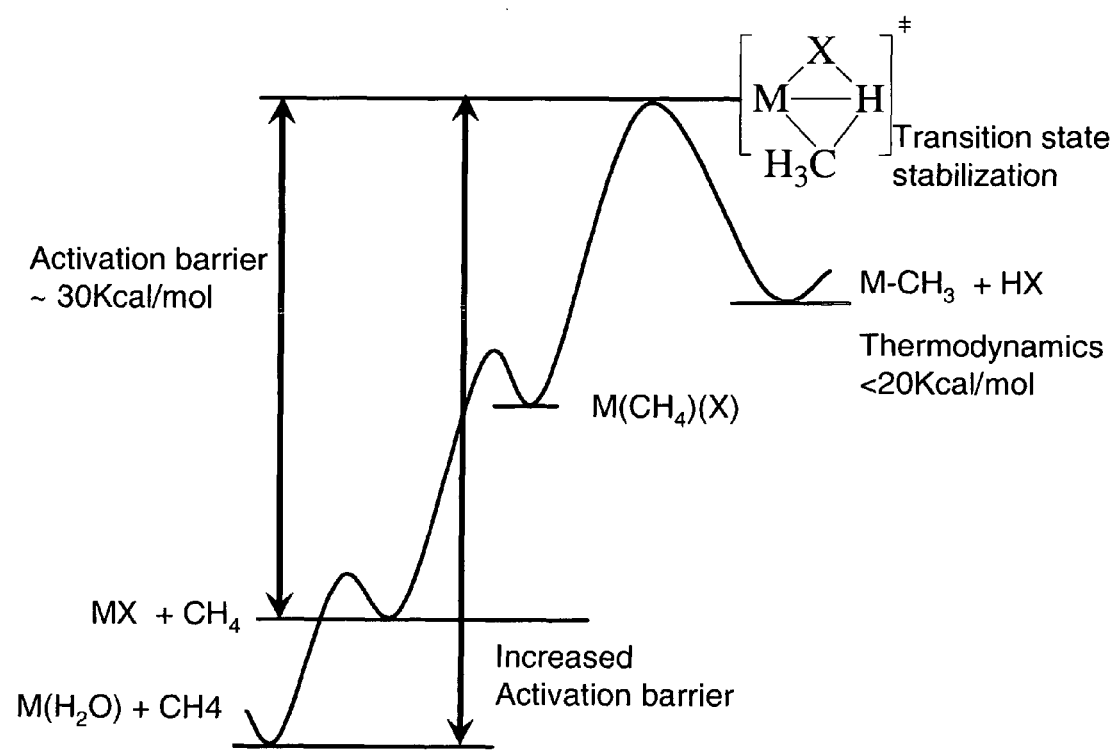
FIG. 1 shows a conceptual energy diagram showing the major contributions to the activation energy for a C—H Activation Reaction.

In order to provide a clearer and more consistent understanding of the specification and the claims, the following definitions are provided:

The term acetylacetonate refers to the conjugate base of 2,4-pentanedione. It is commonly abbreviated acac.

The term "activating" as used herein refers in general to the act of causing a chemical species to be reactive with other chemical species. In a non-limiting example, a catalyst which may be normally inactive or slow to react may be activated by the addition or via contact with another agent.

The term "activating a C—H bond" refers to an overall process whereby a C—H bond and a metal ligand complex, MX, react to generate a metal-alkyl complex comprising a metal-carbon covalent bond (M-C). The reaction can be considered to comprise two steps that are major contributors to the barrier for the overall reaction. The steps are C—H bond coordination to a metal catalyst followed by C—H bond cleavage to yield a metal alkyl complex.

The term "activated by a basic media" refers to rate acceleration of the C—H bond activating step induced by the chemical environment surrounding a metal catalyst according to several embodiments of the invention. A basic medium may be a solvent such as water which is characterized as having pH values greater than 7. Examples of basic media include but are not limited to amines containing the conjugate base amides, alcohols containing the conjugate base alkoxides, water-containing hydroxides. In another embodiment, a basic medium is a molten salt mixture such as NaOH/KOH or $NaNH_2/KNH_2$. In another embodiment a basic medium is a solid support. An example is a basic ion exchange resin. In yet another embodiment, a basic medium is the ligand environment surrounding a metal ion.

The phrase "alcohols containing the conjugate base alkoxides" refers to a pair of compounds related by the loss or gain of a proton. By way of example, methanol, $CH_3OH$ has a conjugate base, methoxide. Such alkoxides have a non-protic counter cation, for example an alkaline earth metal ion. In a like manner, ammonia has a conjugate base, $NH_2^-$, referred to herein as an amide.

The term "alkane" refers to a non-aromatic saturated hydrocarbons with the general formula $C_nH(2_n+2)$, where n is 1 or greater. Alkanes maybe straight chained or branched. Examples include methane, ethane, propane, butane, as well as those which are liquids and solids.

The term "amide" refers to an inorganic derivative of ammonia containing the $NH_2$ anion. The term "amide" may also refers to an organic derivative of ammonia formed by the replacement of one or more hydrogen atoms with acyl groups.

The phrase "amines containing the conjugate base amide" refers to a pair of compounds related by the loss or gain of a proton. By way of example, ammonia, $NH_3$ has a conjugate base, $NH_2^-$. Such amides have a non-protic counter cation, for example an alkaline earth metal ion.

The term "arene" refers to hydrocarbon, the molecular structure of which incorporates one or more planar sets of six carbon atoms that are connected by delocalized electrons numbering the same as if they consisted of alternating single and double covalent bonds. A prototype aromatic compound is benzene. Other examples of arene hydrocarbons are the polycyclic aromatic hydrocarbons composed of more than one aromatic ring.

The term "basic" refers to a functional description of a chemical compound. In one sense, bases are a general class of compounds which accept $H^+$ ions when dissolved in water (a proton acceptor). Also the base may be a Lewis base. A Lewis base is any molecule or ion that can form a new coordinate covalent bond, by donating a pair of electrons.

The related terms, "highly basic", and "super basic" refer to the degree of basicity or alkalinity. In water, the degree of basicity may be measured in units of concentration or equivalents base per unit volume solvent. For aqueous solutions, the degree of basicity may be expressed in pH units. Quantifying basicity or alkalinity in non aqueous solvents is less straightforward, and simple comparisons of base strength in non aqueous solvents are tricky, as they only consider the effect of solvation on the stability of the basic ion or molecule, while neglecting its effects on the stability of the other species involved in the equilibrium. The alkalinity of a particular base may profoundly differ from its value in water. For example, the hydroxide ion is often a much stronger base in nonaqueous solvents (e.g. liquid ammonia, DMSO) than in water. For at least these reasons, a functional definition of basicity is preferable than a numerical quantity that is not transferable between solvents. For example, a superbase is a basic medium in which the basic ion or molecule is only very weakly solvated.

The phrases "basic media" and "non acidic" media as used herein refer to the chemical environment surrounding a metal catalyst according to several embodiments of the invention. A basic or non acidic medium may be a solvent such as water which characterized in having pH values greater than 7. Examples of basic media include but are not limited to amines containing the conjugate base amides, alcohols containing the conjugate base alkoxides, water-containing hydroxides. In another embodiment, a basic medium is a molten salt mixture such as NaOH/KOH or $NaNH_2/KNH_2$. In another embodiment a basic medium is a solid support. An example is a basic ion exchange resin. Other examples include but are not limited to metal oxides such as magnesium oxide, calcium oxide, and barium oxide as well as potassium fluoride on alumina and some zeolites. In yet another embodiment, a basic medium is the ligand environment surrounding a metal ion.

The term "catalyst" as used herein refers to a chemical agent that facilitates a chemical method or process. In one embodiment of the invention, the term is used to describe a reagent used to activate a hydrocarbon C—H bond. In another embodiment, the term refers to a substance that initiates or accelerates a chemical reaction without itself being affected. Catalysts facilitate the chemical reactions between hydrocarbons, oxidants, solvents and other components of a chemical transformation. Coordination catalysts are a class of catalysts that facilitate these reactions by coordination of the reactants within the first coordination sphere of the coordinating atom of the catalyst.

The term "chelating diamides" refers to a metal ligand combination a metal and two amide moieties which form a chelate ring.

The term "chelating diamine" refers to a metal ligand combination a metal and two amine moieties which form a chelate ring.

The term "conjugated π-system" refers to planar an organic compound; containing two or more double bonds each separated from the other by a single bond. Conjugated π-systems may comprise hetero atoms and metal atoms.

The term "feed comprising hydrocarbons and an oxidant" refers to a mixture of hydrocarbon and oxidant entering a reactor. Feed is consumed by a chemical reaction and the result is a desired chemical product. Feed may be processed to extract a desired product or reduced oxidant or it may be recycled.

The term "finely divided solid metal catalyst" refers to catalyst bound to a solid support. The catalyst is finely divided in order to maximize contact area with feed or to facilitate subsequent processing or regeneration.

Figure 14:
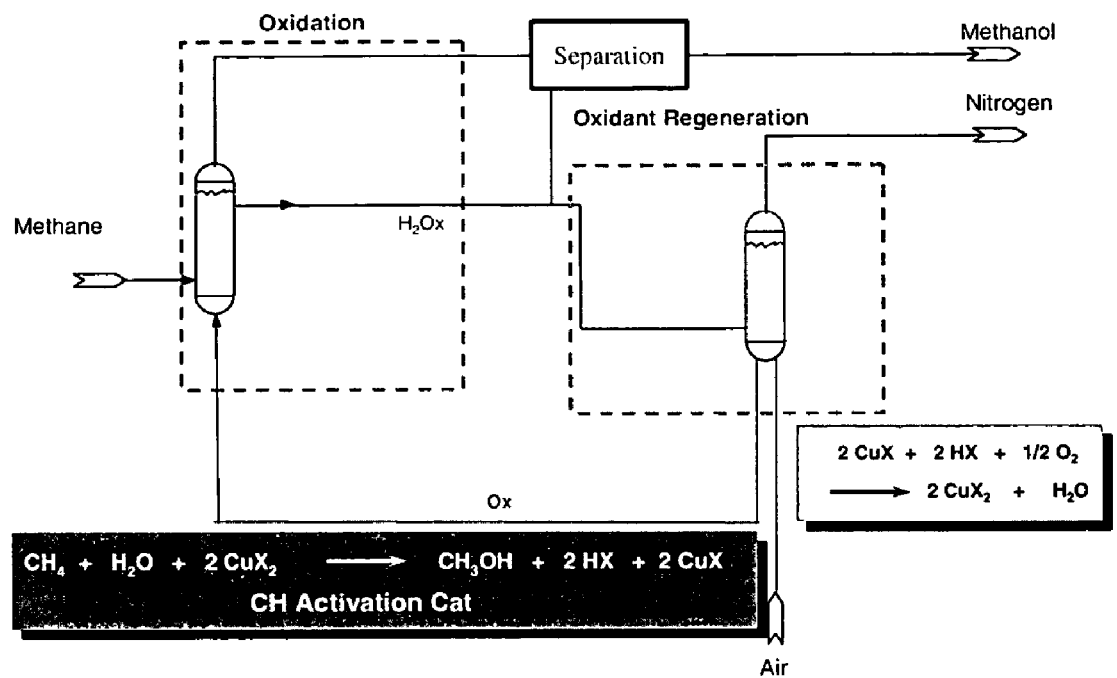
FIG. 14 shows a diagrammatic scheme for a Wacker type air oxidized process.

The term "first catalyst zone" refers to a chemical process reactor. Such a first catalyst zone wherein hydrocarbon C—H bond activation, functionalization, and oxidation occur is shown schematically in FIG. 14. In FIG. 14, the first catalyst zone is distinct from an oxidant regeneration zone where reoxidation of the oxidant occurs. FIG. 14 shows a first reactor zone (indication by dashed lines where hydrocarbon oxidation occurs. According to FIG. 14, methane feed enters a first catalyst zone comprising an activated metal catalyst of the present invention at functionalization conditions. Also present within the first catalyst zone are solvent or solid support. Also shown in FIG. 14 is an oxidant entering a first catalyst zone. After hydrocarbon oxidation occurs according to the generic reaction equation in FIG. 14, effluent leaving the first catalyst zone comprises oxygenated hydrocarbon and reduced oxidant. Oxygenated hydrocarbon is separated from reduced oxidant, and reduced oxidant is passed to a reoxidation zone to reform the oxidant using air as an oxidant. Reoxidation conditions will vary according to the particular oxidant used in Scheme 14. For $CuX/CuX_2$ as shown in FIG. 14, conditions used in the known Wacker process may be used for example to reform the oxidant.

The term "free radical" refers to a molecule having an odd number of valence electrons and may be charged or uncharged (a radical anion or a radical cation) or neutral (free radical) that is not "caged" or strongly controlled by some means and is free to exhibit its intrinsic reactivity.

Figure 29:
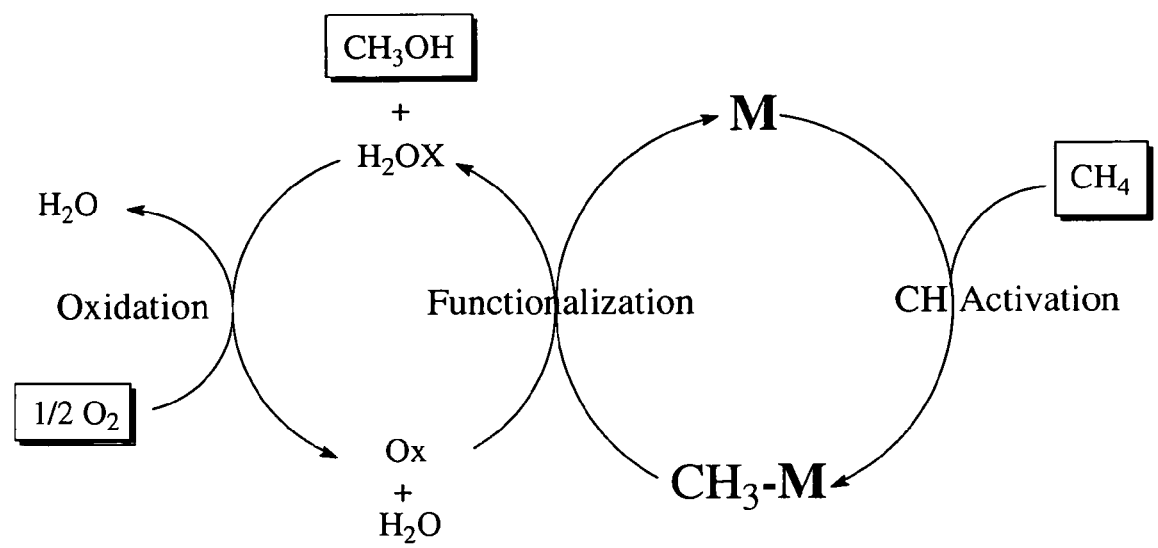
FIG. 29 shows a scheme embodying a process for the selective oxidation of methane to methanol comprising the steps C—H activation, functionalization, and oxidation.

The term "functionalized hydrocarbon" refers to a hydrocarbon wherein at least one C—H bond has been transformed into a carbon functional group bond, a carbon heteroatom bond, where the heteroatom is anything other than H. By way of example only, functionalized methane is methanol. Functionalized benzene is phenol. FIG. 29 for a non-limiting example of how a functionalized hydrocarbon plays a key intermediary role in selective hydrocarbon oxidation.

The term "functionalization conditions" refers to conditions and components required within a first reactor zone to transform a hydrocarbon into a functionalized hydrocarbon. Functionalization conditions include the type of metal ligand complex, solvent, temperature, and oxidant. In one embodiment the metal is selected from the group consisting of Re, Os, Ir, Ru, and W. The oxidation state of suitable metals is intermediary, neither the highest oxidation state, nor metallic. Oxidation states Os(II), Ru(II), Re(I), Ir(III) in basic solvents are suitable. Suitable ligands are oxidation resistant and include but are not limited to acetylacetonate (acac), tropolone, aryloxide, catechol, hydroxyacetophenone, e.g., 2-acetyl phenol.

The term "Gibbs free energy value" refers to a thermodynamic quantity. The Gibbs free energy is a thermodynamic potential which determines outcomes such as the voltage of an electrochemical cell, or the equilibrium constant for a reversible reaction. An equilibrium so characterized by experiment or computationally has a corresponding value, ΔG, which is equal to a change in Gibbs free energy.

The term "Group IV" refers to the elements carbon, silicon, germanium, tin, and lead.

The term "Group V" refers to the elements nitrogen, phosphorus, arsenic, antimony, and bismuth.

The term "Group VI" refers to the elements oxygen, sulfur, selenium, tellurium, and polonium.

The term "hydrocarbon C—H bond" as used herein refers to a covalent bond between hydrogen and carbon localized within a hydrocarbon molecule. A C—H bond may be described in terms of frontier molecular orbital theory as having a highest occupied molecular orbital (HOMO) and a lowest unoccupied molecular orbital (LUMO).

The phrase "hydrocarbon activation is accelerated by solvent" refers to a rate increase due to solvent which is predicted or observed for a C—H bond activation event.

The phrase "identifying hydrocarbon activation catalysts" refers to a screening method for predicting the identity of catalysts useful for hydrocarbon activation.

The term "ligand" as used herein refers to the set of atoms, ions, or molecules in contact with a metal ion. Ligands comprises the set of atoms, ions, or molecules surrounding a metal ion in the first coordination sphere of the metal. Free ligands may be indistinguishable from solvent molecules.

The term "ligating atom" as used herein refers to atom or atoms comprised by a ligand which bind to a metal. "Ligating atom is equivalent to "donor atom" in certain embodiments.

The term "linked nitrogen heterocycle" refers to bipyridine, bipyrazine, bipyrimidine and the like.

The term "metal alkoxide" refers to an organic group bonded to a negatively charged oxygen atom, which is in turn bonded to a positively charged metal ion or metal ligand complex. A metal alkoxide also refers to a conjugate base of an alcohol and a metal ion.

The term "metal-alkyl covalent bond" refers to an alkyl group bonded to a transition metal or metal complex.

The term "metal alkyl complex" refers to an alkyl group bonded to a metal complex.

The term "metal hydroxy complex" refers to a hydroxy group bonded to a metal complex.

The phrase "metal aquo complex in aqueous solution" refers to a metal complex having a bound water molecule as a ligand.

The term "metal chelate" refers to a metal ligand combination comprising a metal and at least two Group IV, Group V, or Group VI ligating atoms moieties which form at least one chelate ring.

The term "molten salt mixtures" such as NaOH/KOH or $NaNH_2/KNH_2$ refers to mixtures of salts reduced to liquid form by heating.

The term "nitrogen heterocycle" refers to organic compounds that contain a ring structure containing nitrogen atoms as part of the ring. They may be either simple aromatic rings or non-aromatic rings. Some examples are pyridine, pyrimidine, and pyrazine.

The term "non-radical producing" as used herein refers to a method or process characterized by the absence of free radical. Such radicals may be oxygen-based, carbon based, or metal based.

The term "O-atom donor" refers to any O-atom donor that has a potential to thermodynamically oxidize methane to methanol at a temperature of 300° C. or lower. Thermodynamic potentials for methane oxidation may be calculated from the equation:

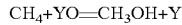

$$CH_4 + YO = CH_3OH + Y$$

The change in Gibbs free energy for this reaction, $\Delta G_{rxn}$, determines whether an O-atom transfer donor has the potential to thermodynamically oxidize methane. Values $\Delta G_{rxn} < 0$ based on calculated or tabulated data for the equation: $CH_4 + YO = CH_3OH + Y$ indicate the conversion of methane is feasible. An approximation of the $\Delta G_{rxn}$ may be obtained by considering the bond strengths of the reactants and products. On this basis any oxidant (YO) with Y—O bond strength of less than about 90 kcal/mol is a candidate O-atom donor.

The term "O-donor atom" refers to ligand or solvent molecules which bind directly to metals according to certain embodiments of the invention. O-donor atoms may be part of O-donor ligands. Suitable O-donor ligands include acetylacetonate (acac), tropolone, aryloxide, catechol, and hydroxyacetophenone, e.g., 2-acetyl phenol.

The term "oxidant" refers to a compound that oxidizes (removes electrons from) another substance in a chemical oxidation, reaction, process or method. In doing so, the oxidizing agent, sometimes called an oxidizer or oxidant, becomes reduced (gains electrons) in the process. An oxidizing chemical reaction is a broadly defined and may have several meanings. In one definition, an oxidizing agent receives (accepts) electrons from an other substance (reductant). In this context, the oxidizing agent is called an electron acceptor. Broadly speaking, such chemical events occur in two distinct ways which can be described as inner sphere or outer sphere. In another meaning, an oxidant transfers O atoms to the reductant. In this context, the oxidizing agent can be called an oxygenation reagent or oxygen-atom transfer agent. Examples include amine-N-oxide, cupric oxide, iron oxide, periodate ($IO_4^-$), vanadate ($VO_4^{3-}$), molybdate ($MoO_4^{2-}$), nitrous oxide ($N_2O$), hydrogen peroxide ($H_2O_2$), selenate ($SeO_4^{2-}$), tellurate ($TeO_4^{2-}$), hypochlorite ($ClO^-$), chlorite ($ClO_2^-$), nitrate ($NO_3^-$), and sulfoxide.

The term "oxidation stable solvent" refers to a solvent that is not itself oxidized during any step of a chemical reaction, method, or process.

The term "oxygen insertion agent" refers to an agent which functions as both an oxidant and as a source for an oxygen atom which inserts into a metal-alkyl covalent bond. Examples include Examples include amine-N-oxide, cupric oxide, iron oxide, periodate ($IO_4^-$), vanadate ($VO_4^{3-}$), molybdate ($MoO_4^{2-}$), nitrous oxide ($N_2O$), hydrogen peroxide ($H_2O_2$), selenate ($SeO_4^{2-}$), tellurate ($TeO_4^{2-}$), hypochlorite ($ClO^-$), chlorite ($ClO_2^-$), nitrate ($NO_3^-$), and sulfoxide.

The term "oxygenated hydrocarbon" refers to a hydroxylated hydrocarbon. Methanol is an oxygenated hydrocarbon (methane).

The term "oxidation resistant ligands" refers a ligand(s) that is not itself oxidized during any step of a chemical reaction, method, or process.

The term "pH value" refers to a measure of the activity of hydrogen ions (H+) in a solution and, therefore, its acidity or alkalinity. Aqueous solutions with pH values lower than 7 are considered acidic, while pH values higher than 7 are considered alkaline.

The term "polyamide" refers to organic compounds, that have two or more primary amido groups.

The term "polyamine" refers to organic compounds, that have two or more primary amino groups.

The term "polyol" as used herein refers to organic compounds, that have two or more primary alcohol groups.

The term "radical" refers to a molecule having an odd number of valence electrons and may be charged or uncharged (an anion or a cation) or neutral (free radical). Radicals are generally more reactive than molecules with an even number of electrons. Radicals, especially oxygen and halogen based free radicals may react with hydrocarbon C—H bonds, but do so with a reactivity selectivity tertiary C—H bond>secondary C—H bond>primary C—H bond. The C—H bonds of methanol and other functionalized products can be more susceptible, relative to the feed alkane hydrocarbon, to reaction with free-radicals and can thus be destroyed at a higher rate than its formation in a reaction involving free radicals. For this reason, processes which rely on free radical reactions to cleave the C—H bond would not be expected to be useful for selectively oxidizing alkanes having primary C—H bonds like methane to generate products such as alcohols.

The term "reduced oxidant" refers to an oxidant which has transferred an O atom during or as a consequence of an alkane functionalization process. By way of example, for the oxidant $SeO_4^{2-}$, the reduced oxidant is $SeO_3^{2-}$.

The term "regenerating the catalyst" refers to a step during a process for selective oxidation of hydrocarbons. During this step, a reduced oxidant is reoxidized into an oxidant or an oxygen insertion agent. Preferred reoxidizing agents are air or dioxygen ($O_2$). Suitable oxidants are those that can be reoxidized with air in a thermodynamically favorable reaction: $Y+\frac{1}{2}O_2 \rightarrow YO$ where $\Delta G_{rx,n} < 0$ kcal/mol at temperatures below 300° C. On the basis of tabulated data, the following examples are given by way of example only.

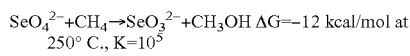

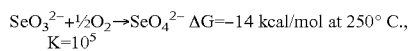

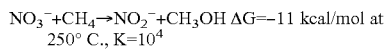

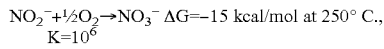

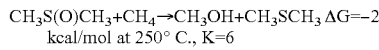

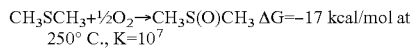

The term "reoxidation zone" refers to a second reaction used to regenerate an oxidant. FIG. 14 depicts a reoxidation zone according to one embodiment. In FIG. 14, a reoxidation zone receives a reduced oxidant which is reoxidized using air to oxidant.

The term "reoxidizing conditions" refers to conditions and components required within an reoxidation zone to transform a reduced oxidant back into an oxidant. Reoxidizing conditions will vary according to the particular oxidant used in Scheme 14. For $CuX/CuX_2$ as shown in FIG. 14, conditions used in the known Wacker process may be used for example to reform the oxidant.

The term "releasing an oxidized hydrocarbon" refers to a step during a process for selectively oxidizing hydrocarbons as disclosed herein. During this step, an oxidized hydrocarbon is released from a metal.

The term "selectively oxidizing" refers to C—H bond selectivity exhibited by a catalyst during C—H bond activation and subsequent steps. Selective oxidation occurs for example when a catalyst selects a primary versus a secondary or tertiary C—H bond. Selectivity can also occur when a catalyst selects an alkyl C—H bond of an unreacted hydrocarbon versus that of an oxidized or functionalized hydrocarbon.

The term "solid support" refers to an insoluble matrix to which a catalyst or catalyst complex is attached. An example is a basic ion exchange resin. Other examples include but are not limited to metal oxides such as magnesium oxide, calcium oxide, and barium oxide as well as potassium fluoride on alumina and some zeolites.

The term "solvent assisted" refers to the role a solvent molecule plays in reaction energetics of a C—H bond activating step. A consequence of solvent assistance is an increased reaction rate a C—H bond activating step and an overall hydrocarbon oxidation process.

The term "transition metal ion." as used herein refers to any of the transition elements (i.e. the elements Sc through Cu, Y through Ag, La, Lu through Au), especially W, Re, Os, Ir, Rh, and Ru.

The present invention embodies a class of catalysts that can selectively oxidize hydrocarbons to useful products such as alcohols by the use of late, electron-rich metals such as Os(II), Ru(II), Re(I), Ir(III) in basic solvents. Several concepts provide the basis this embodiments of the present invention. Among them are:

I) Specific metals in selected oxidation states can be "activated" (made more reactive) in basic solvents;
II) Such metals can be used to catalyze the oxidation of hydrocarbons to products such as alcohols;
III) O-donor ligands are effective in these reactions;
IV) Selected oxidants that are stable in basic media are effective and those that can be recycled with air are particularly useful;
V) Metal-hydroxides and metal-alkoxides are effective catalysts;
VI) Developing catalytic cycles based on C—H activation of hydrocarbons RH, with M-OY (where Y is H or R) to generate YOH and M-R, followed by O-atom insertion is an effective cycle for catalytic conversion of alkanes to alcohols.

Certain embodiments of the present invention may be understood by insights gained from studies of systems which operate in strongly acid media. These insights are not intended to be an admission of knowledge prior to the date of disclosure of the inventions disclosed herein.

Figure 2:
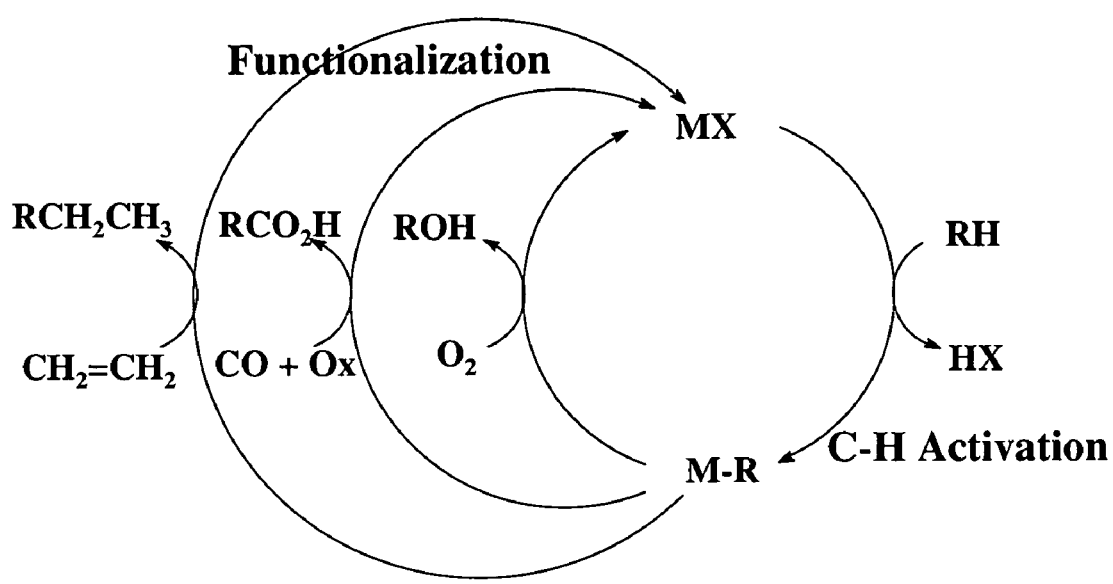
FIG. 2 shows the use of the C—H bond activation reaction for developing catalysts for hydrocarbon oxidations.

Subsequent studies of systems which operate in strongly acidic media have shown that those systems operate efficiently in strong acids because the catalysts facilitate C—H activation reaction in acidic media. As shown in FIG. 1, the reaction proceeds via the cleavage of the C—H bond and generation of a metal alkyl complex, M-CH₃ as an intermediate. As can be seen, C—H activation is composed of two discrete steps that contribute to the activation barrier; substrate coordination and C—H cleavage. Since breaking the C—H bonds of hydrocarbons at lower temperatures is key to developing efficient catalysts that operate at lower temperatures, minimizing the energy of the two steps involved in breaking the C—H bond is important in reducing the activation barrier to the C—H activation reaction. Both steps can contribute significantly to the overall barrier and reducing one or both can lead to the generation of efficient catalysts. The C—H activation reaction is useful since this reaction occurs rapidly at lower temperatures, is highly selective and can be coupled with functionalization reactions into catalytic sequences as generally shown in FIG. 2, for the generation of useful products such as alcohols, carboxylic acid, etc.

Pt(II) and Hg(II) are useful as catalysts since these metals are electronegative and "soft" and form relatively strong covalent bonds to carbon. This is important, since as can be seen in FIG. 1, the overall thermodynamics for the C—H activation reaction from the reaction of MX with a C—H bond to generate a metal alkyl complex product would set the minimum activation barrier for the reaction. Since the third and second row metals form the strongest bonds to carbon, many of the these elements, e.g. Au, Pd, Tl have been shown to react with methane. Pt(II) and Hg(II) are examples of methane oxidation catalysts that are activated by highly acidic solvents. The importance of this solvent activation is demonstrated by the observation that both Hg(II) and Pt(II) only react with alkanes in strongly acidic media; in less acidic, none acidic or basic media these metals do not react with hydrocarbons or do so at impractically slow rates. Indeed, a major disadvantage of the Pt(II) or Hg(II) catalyzed $H_2SO_4/CH_4$ systems was that only ~1M methanol could be developed before the reaction effectively stopped due to the effective drop in solvent acidity. This product inhibition leads to impractically high separation costs. The primary reason for this limitation in product concentration is that as both the methanol and water build up in the reaction mixture, these molecules preferentially coordinate to the Hg(II) ions and inhibit catalysis.

A key to the activation of Pt(II) or Hg(II) in strong acids is the replacement of tightly coordinated ligands to the metal, e.g., water or alcohol, with more weakly bound conjugate anions of the acid solvent, $X^-$ as shown in Eq 1.

$$LPt(H_2O)+X^- \rightarrow LPtX^- +H_2O \quad \Delta G_1>0 \quad \text{Eq 1}$$

This results in a more reactive, or "activated" catalyst. To understand why requires consideration of the role of the acid solvent. In Eq 1, if $X^-$ is the conjugate anion of a strong acid, it is a poor nucleophile, and would thus be less tightly coordinated than water to electronegative metals. The $LPtX^-$ species would be higher in energy and thus activated. The reaction as shown in Eq 1 is thus "uphill and $\Delta G_1>0$.

As a consequence of its higher free energy, $LPtX^-$ is more reactive than $LPt(H_2O)$. Alkane activation with $LPtX^-$ (Eq. 2 below) would show lower activation barriers than alkane activation with $LPt(H_2O)$ (Eq 3 below). Stated yet another way, Eq 2 would be expected to be more favorable (requires less energy) than Eq 3.

$$LPtX^- + CH_4 \rightarrow LPt(CH_4) + X^- \quad \Delta G_2>0 \quad \text{Eq 2}$$

$$LPt(H_2O)+CH_4 \rightarrow LPt(CH_4)+H_3O \quad \Delta G_3>0, \Delta G_2<\Delta G_3 \quad \text{Eq 3}$$

$$LPt(H_2O)+HX \rightarrow LPtX^- +H_3O^+ +X^- \quad \Delta G_4 \leq 0 < \Delta G_1 \quad \text{Eq 4}$$

This can be seen visually in FIG. 1, where it can be seen that starting from the higher energy (less stable) MX species leads to a lower activation barrier than staring from the $M(H_2O)$ species. Indeed, theoretical calculations show that the difference in energy between these species is ~7 kcal/mol for the Pt bipyrimidine catalyst. This large stabilization of the catalyst ground state leads to orders of magnitude differences in catalytic activity. This explains the impractically slow rates of reaction of Pt(II) in the presence of water or other weak acids or bases and rapid reaction in strong acid solvents.

Coordination catalysis including C—H activation is a very efficient form of catalysis because the bond rearrangements of the substrates to products are mediated within the first coordination sphere of another atom or atoms that constitute the catalyst. This is useful because the reactants are "controlled" by the catalyst throughout the transformation since the reactants are bonded to the catalyst. This is in contrast to reactions where the reactants are generated as "free" species with intrinsic reactivity that cannot be controlled, e.g. "free" radical, solvent separated carbocations, carbanions or carbenes. Additionally, since energy is released in making bonds to the catalyst in coordination catalysis this can compensate for the energy required to break strong bonds in the substrate. Acid and base chemistry are examples of coordination catalysis involving protons and bases, where the chemistry occurs within the coordination sphere of these catalysts. In most acid and base catalyzed reactions, the substrates involved, olefins, carbonyl, arenes, alcohols, etc. are very good coordination species and can readily coordinate to protons or bases. However, a key challenge in hydrocarbon chemistry, especially alkanes, is that these species are among the poorest ligands known. Indeed, while coordination metal complexes of almost all functional classes of molecules are known, stable alkane complexes have not yet been generated. A consequence of this is that efficient coordination catalysis of the alkanes has not yet been developed.

Another challenge to developing coordination catalyst for the conversion of alkanes to alcohols is that alcohols are much more coordinating than alkanes. Thus, many coordination catalysts preferentially bind alcohols rather than alkanes. This becomes problematic because the product alcohol can inhibit the alkane conversion catalyst. Alcohols are similar to water in basicity and coordinating capability and alcohols can be readily dehydrated to generate water. Additionally, in many circumstances it is desirable to carry out coordination catalysis in a solvent and in many cases the desirable solvents are protic substances such as water, acids, bases, etc. Consequently, designing catalysts that are not inhibited by water is one of the central challenges to developing catalysts that efficiently oxidize alkanes to alcohols.

Figure 3:
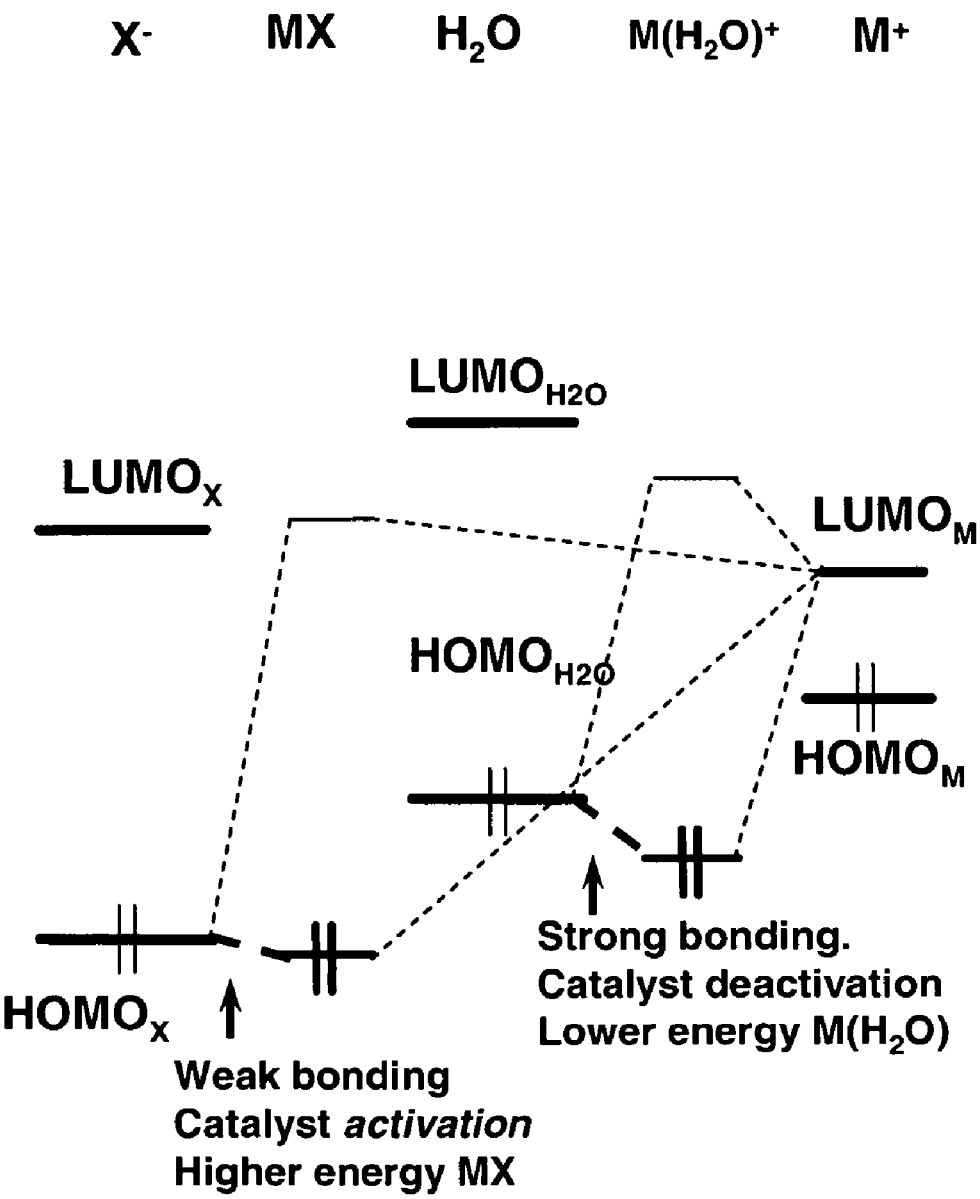
FIG. 3 shows an Energy Diagram showing $H_2O$ and $X^-$ HOMO Interactions with the LUMO of $M^+$

Frontier Orbital Diagrams and supporting calculations provide a basis for predicting broad classes of compounds and their reactivities. FIG. 3 depicts the interaction of the frontier orbitals (LUMO and HOMO) of the $M^+$ ion with ligands, L, $H_2O$ and the anion $X^-$, of a strong acid such as $HSO_4^-$. The key points illustrated in FIG. 3 are that the primary interaction between $M^+$ and these ligands is with the LUMO of $M^+$ and the HOMO of L. This is characteristic of so-called "electrophilic" catalysts, wherein this frontier orbital interaction is more important than the other possible interaction, the LUMO of L and the HOMO of $M^+$ are not as important. As expected on the basis of known relative electronegativities of atoms and basicities of $H_2O$ and typical $X^-$ species, the HOMO of water is expected to be higher than that of $X^-$. This leads to stronger interaction of the electrophilic catalyst LUMO with water, stronger binding and lower energy of the $M(H_2O)$ complex and lower reactivity and lower catalyst rates relative to MX species. The HOMO of $X^-$ is lower in energy and would interact less with $M^+$ resulting in a higher energy, more reactive species. FIG. 3 is fully consistent with the relative orders of stabilities depicted in FIG. 1.

Figure 30:
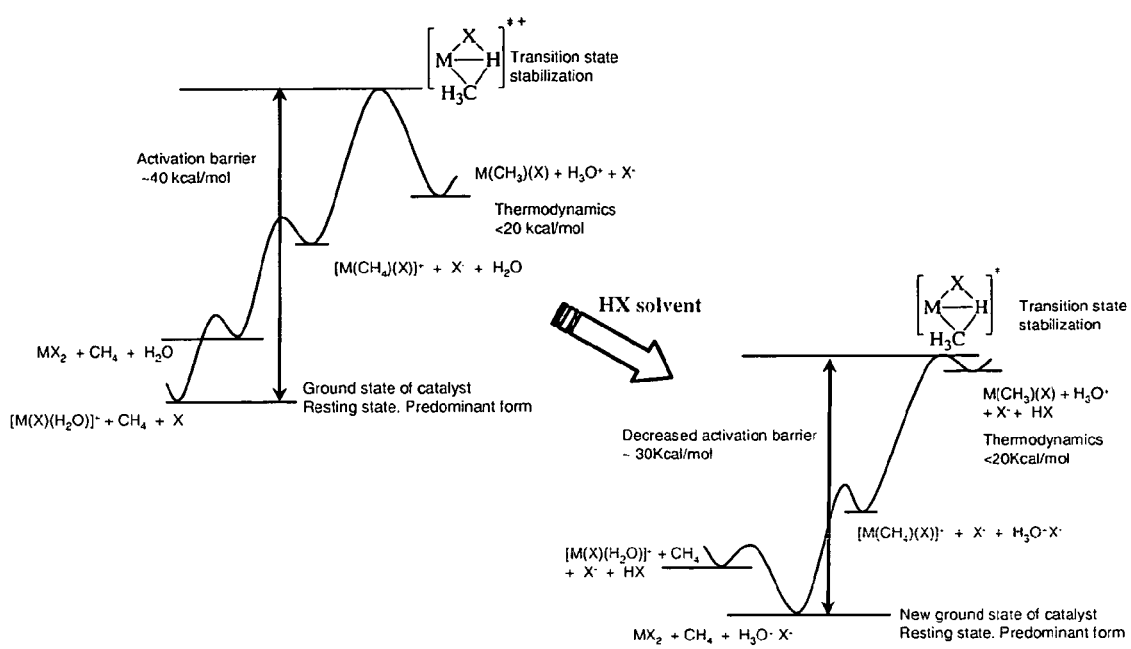
FIG. 30 Shows the effect of solvent activation on the energy profile for C—H activation.

Importantly, while LPtX is expected to be more reactive on the basis of these considerations, its equilibrium concentration based on Eq 1 would be expected to be negligible for the same reason that it is more reactive; it is less stable. Consequently, under the conditions of Eq 1 where water is present in the system, LPtX would not be an important species in catalysis, i.e., it would not be one of the predominant forms of the catalyst and would not influence the reaction rates. The key to favoring catalysis with LPtX is that in acid solvents, the equilibrium reaction is best described by Eq 4 (as verified with QM calculations). In this case the reaction is favorable for the generation of LPtX, $\Delta G_4<0$, because of mass action (HX is the solvent) and also protonation of the free water by the acid solvent (the hydration energy of $H_2SO_4$ is ~−22 kcal/mol and LPtX can become an important catalytic species. Thus, under conditions of Eq 4, in the presence of HX as the solvent, the reaction diagram shown in FIG. 1 would be considered from the MX species, since under these conditions MX is the catalyst resting state either because $M(H_2O)$ is not present or both species are present in comparable concentrations. Thus, the net result is that in acidic solvents the catalyst is "activated" to a more reactive state, the LPtX species. These aspects are illustrated in FIG. 30.

In addition to the ground state (the most stable state of the catalyst), FIG. 1 indicates other considerations important to developing catalysts that operate via the C—H activation reaction. These include considerations of the energy barrier or transition state for C—H cleavage as well as the stability of the C—H activation product M-C. When all these factors are considered, as well as the requirement that the metals allow functionalization to alcohols to proceed, the ideal catalyst are species that:

A) do not bind strongly to water or related oxygen species,
B) form strong covalent bonds to carbon,
C) exhibit low energy requirements for the changes in electronic configuration needed to stabilize the various structures along the reaction path and
D) can access different oxidation states reversibly.

Highly basic solvents (e.g., $NaOH/H_2O$ solutions, and eutectic molten salt melts of MOH such as NaOH/KOH, $NH_3$, etc.) are desirable materials for hydrocarbon oxidation to such products as alcohols because they are:

A) inexpensive;
B) can be moderated with water;
C) water can be removed under appropriate conditions;
D) basic solvents can strongly interact with and activate catalysts;
E) can dissolve suitably designed catalysts; and
F) can "protect" oxidation products, e.g., alcohols to further oxidation.

One aspect of the present invention is the realization that selected metal ions that are electropositive can be activated (generate more reactive species) toward the C—H activation reaction in basic media rather than be inhibited. As in the case of the Pt(II) and Hg(II) systems a critical issue will be preventing catalyst inhibition by preferential coordination to water or alcohol products that can increase the barriers to C—H activation.

Figure 4:
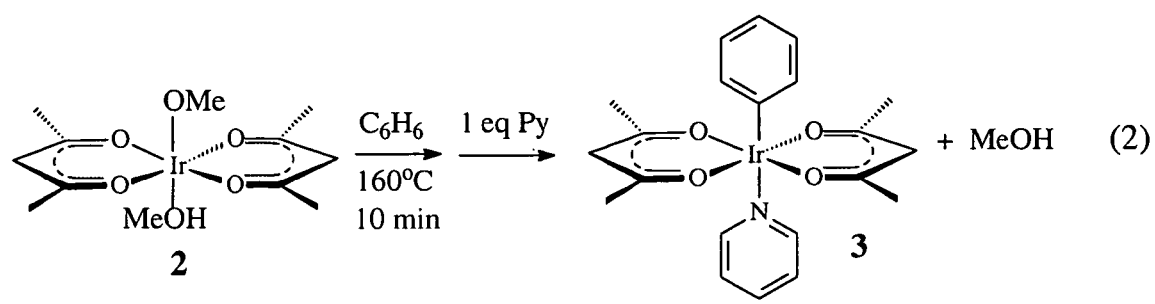
FIG. 4 shows an example of hydrocarbon activation according to one embodiment of the invention.

FIG. 4 depicts one embodiment of the present invention. FIG. 4 depicts the C—H activation reaction with an M-OH species. As in the case for an MX species, key considerations are the energy for alkane coordination, the barrier to cleavage, and the thermodynamics for M-C formation. On the basis of metal-carbon bond strengths, we consider that metal ions of the second and third row metals are particularly suitable embodiments.

In basic media such as $OH^-/H_2O$ or $O^{2-}/OH^-$, $CH_3O^-/CH_3OH$, etc. the composition of the metal ligand complex comprises M-OY, where OY is the conjugate base of the basic solvent; $OH^-$ when the solvent is water, $O^{2-}$ when the solvent is NaOH/KOH molten salt, $CH_3O^-$ when the solvent is $CH_3OH$. Thus, Y will be electron donating groups such as H, R, alkali metals. As indicated above, the reaction of M-X species where X is electron-withdrawing is precedented in acid media. A key to developing catalysts that react with alkanes in basic media is the requirement for the reaction of M-OY, Y=electron donating group such as H, R, alkali metals, Si, B, etc. with hydrocarbons, RH, to generate the C—H activation product, M-R and the corresponding product, YOH.

Precedent for this type of reaction of M-OY, where OY Y═H and Y═alkyl or aryl. The Ir—OMe metal ligand complex depicted in FIG. 4 reacted with neat benzene below 200° C. to generate the Ir-Ph species and MeOH (see Term et al. *J. Am. Chem. Soc.* 2005, 127(41), 14172 and complete experimental details reported therein). This observation is an example of a C—H bond activation reactions with M-OY species, where OY is basic rather than acidic. In this case, the basic OY group is a methoxy group which is the conjugate base of methanol.

The C—H bond activation process in FIG. 4 is distinct from those carried out with Hg(II) or highly electrophilic cations. This IR(III) methoxy system serves as a precedent for the reaction of M-OH species since this system catalyzed H/D exchange between benzene-$H_6$ and $D_2O$.

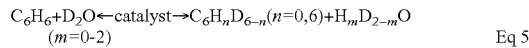

Figure 5:
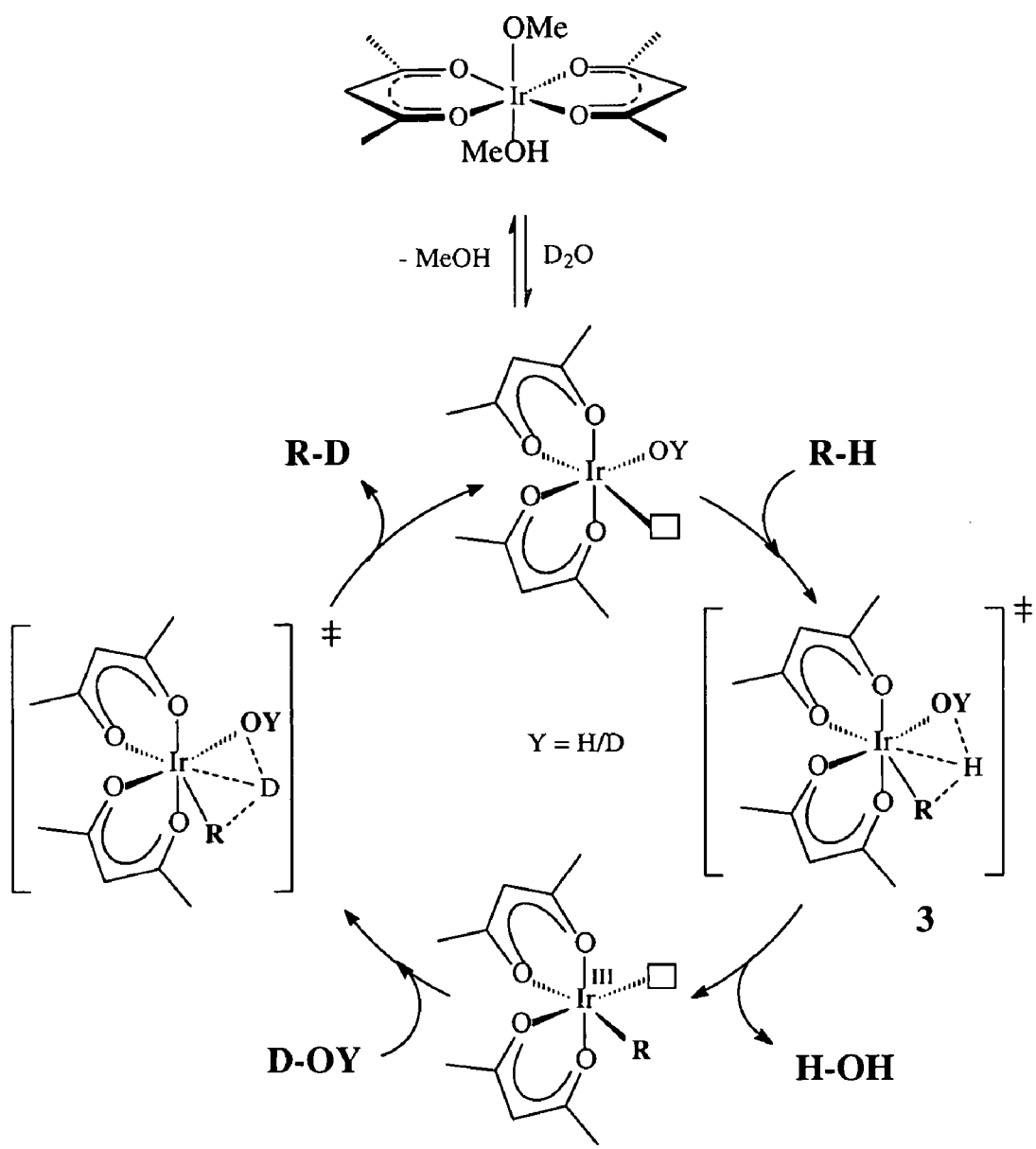
FIG. 5 shows an example of hydrocarbon activation and H/D exchange according to another embodiment of the invention.

When the Ir—OMe complex depicted in FIG. 5 was dissolved in water, the loss of OMe and MeOH groups are observed and the $(acac)_2Ir(OH)(H_2O)$ complex was the expected product. Thus, this exchange between $D_2O$ and $C_6H_6$ is evidence and precedence for C—H activation with M-OH species. Experimental and theoretical calculations indicate that the barrier to this exchange is ~30 kcal/mol. The aforementioned method of observing H/D exchange comprises a method of identifying hydrocarbon C—H bond activation catalysts in non acid media.

Pt(II) and Hg(II) systems are strongly inhibited by basic media. Thus, considering the following equilibria for Pt(II), Eq 6 and Eq 7, it can be shown that Eq 6 is favorable while Eq 7 would much less favorable than either Eq 3 or even Eq 4. This explains why, as observed, both Hg(II) and Pt(II) are strongly inhibited by basic solvents. Indeed, a characteristic of these late, electronegative metal cations is that the M-OH species are acidic and favorably react further with $OH^-$ to generate even more stable MO species (Eq 8) that are less reactive than the M-OH species with methane, i.e., Eq 9 is less favorable than Eq 6 or Eq 7.

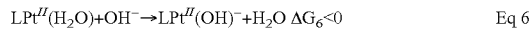

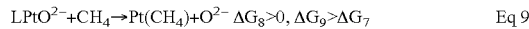

Metals that will be activated by basic solvents are second and third row late transition metals hydroxides, LM-OH, that are thermodynamically less stable, Eq 10, $\Delta G_{10}>0$, than the corresponding aquo complexes, Eq 6, $\Delta G_9<0$. Such M-OH species would be expected to increase the basicity of water and this could serve as a method of identifying suitable second and third row transition metal hydroxides as candidate catalysts. Such LM-OH complexes that react with C—H bonds are more reactive than the corresponding $LM(H_2O)$ species.

The method of measuring or calculated $\Delta G$ values comprises a method of identifying new hydrocarbon C—H bond activation catalyst candidates.

The reason that $Hg^{II}$—OH and $Pt^{II}$—OH are more stable than the corresponding aquo complexes, $Hg^{II}(H_2O)$ or $Pt^{II}(H_2O)$ is for the same reason that the $M(H_2O)$ complexes were more stable than the MX complexes. These metals are highly electronegative and form stronger bonds to better sigma electron donors such as $OH^-$ over $H_2O$ or $X^-$ (an anion of a strong acid) that are weaker donors. This is easily conceptualized if we add $OH^-$ interactions to FIG. 3 to obtain FIG. 6. As can be seen, the higher HOMO of $OH^-$ leads to greater interaction with the LUMO of $M^+$ than either $H_2O$ or $X^-$.

Figure 6:
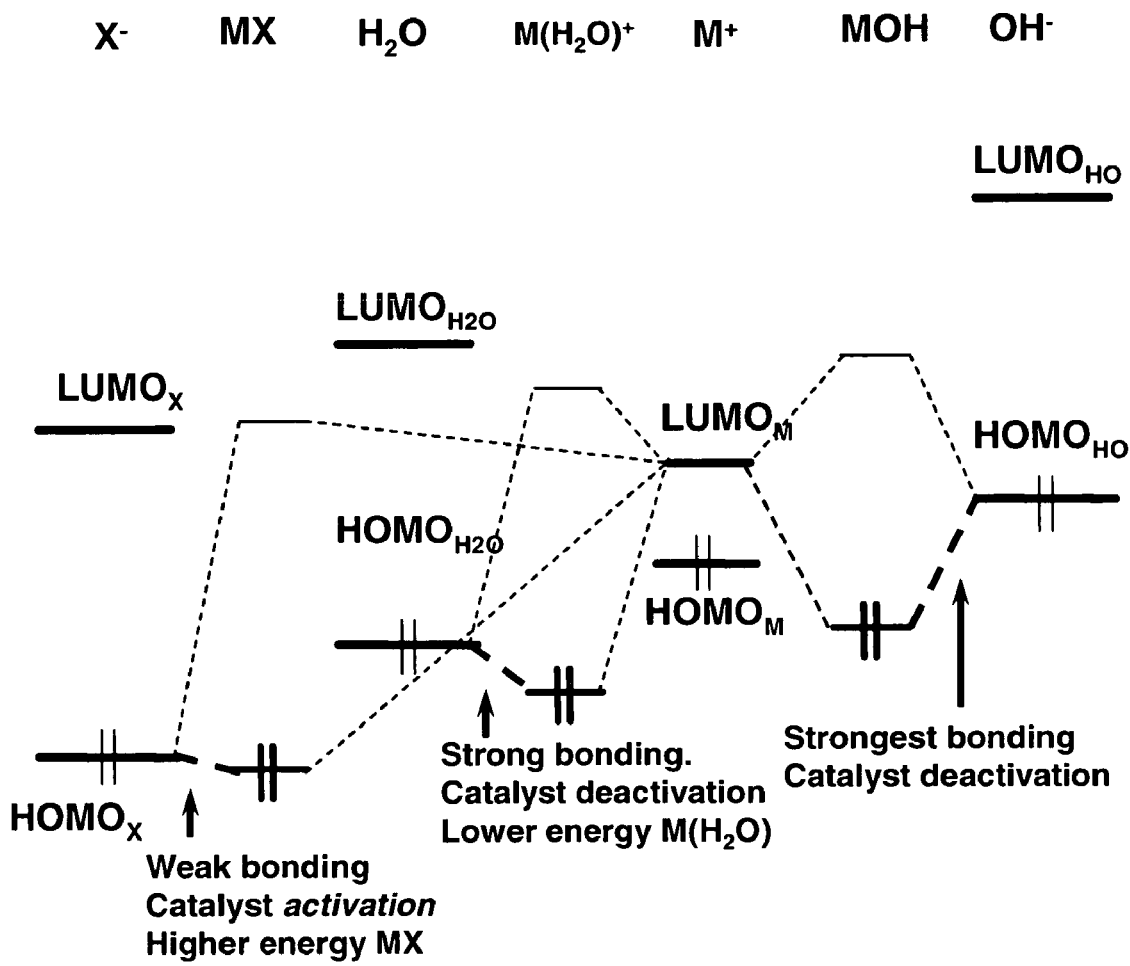
FIG. 6 is an energy diagram showing $H_2O$, $X^-$ and $OH^-$ HOMO interactions with the LUMO of $M^+$
Figure 7:
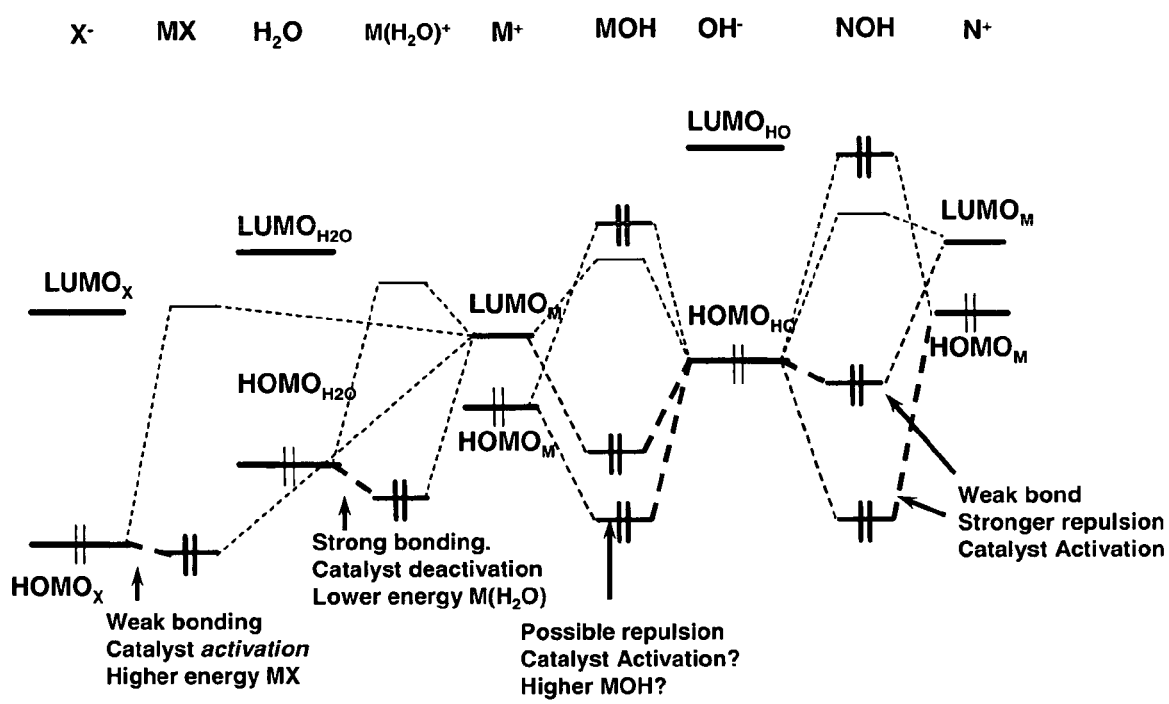
FIG. 7 is an energy diagram showing possible $OH^-$ HOMO LUMO interactions with the HOMO and LUMO of $M^+$ and a metal catalyst of invention, $N^+$.

However, FIG. 6 also shows interaction that can weaken the bonds to $OH^-$ or $H_2O$ more than with $X^-$. This is because, in addition to bonding interactions between the $M^+$ LUMO and ligand HOMO, there is a destabilizing $M^+$ HOMO to ligands HOMO interactions as shown in FIG. 7. In the case of Hg(II) this HOMO-HOMO interaction is much less important than for Pt(II) since the HOMO of Hg(II) is a filled $5d^{10}$ shell and is much lower in energy than the HOMO of $H_2O$ or OH⁻. However, in the case of Pt(II), a transition metal (valence shell are d-type orbitals, $d^8$ metal), the HOMO and LUMO are both d-orbitals and the $M^+$ HOMO to ligand HOMO becomes important. Thus, whether the LPtOH metal ligand complex is more stable than the LPt(H$_2$O) complex depends on a complex interplay of LUMO/HOMO favorable interactions and HOMO/HOMO repulsions that can change depending on the geometry of the complexes, the ligands and energies of these various orbitals. Given this increased complexity of electronic interactions that must be considered, theoretical calculations are required for good predictive accuracy.

As seen in FIG. 7, if a new metal species, designated as $N^+$, is chosen such that both the LUMO and HOMO are increased in energy relative to $M^+$, then the bonding interactions between $N^+$ LUMO and OH⁻ HOMO will decrease while the repulsive $N^+$ HOMO to OH⁻ HOMO will increase. In such a case, the interactions between $N^+$ and OH⁻ are weaker than the interactions with H$_2$O and the reaction of N(H$_2$O)$^+$ with OH⁻ is uphill and systems that meet the requirement for Eq 10 can be developed.

While the equilibrium shown in Eq 10 can be calculated to determine which N—OH are less stable than the N(H$_2$O)$^+$ complexes according to one embodiment of the invention, a conceptual basis for selection is also possible. On the basis of known periodic trends, the metals to the left of the periodic table are more electropositive, less electronegative than those on the right as a result of increased effective nuclear charge of the elements the right. This trend in decreasing electronegativity in moving to the left can be observed in increasing HOMO LUMO levels. Thus, as discussed above, on the basis of FO considerations, it can be anticipated that N—OH species to the left will be increasingly less stable relative to the N(H$_2$O)$^+$ than those to the right.

This general prediction is also consistent with the known acidities of metal aquo complexes, Eq 11. Thus, it is known that metal aquo complexes are more acidic than those to the left. Thus, e.g., Hg$^{II}$(H$_2$O) would be expected to be acidic in water and Eq 11 and $\Delta G_{11} < 0$ for this ion. In this case, Eq 9<0 for Hg$^{II}$ and the M—OH is more stable than the N(H$_2$O) complex. However, as one moves to the left on the periodic chart, e.g. Os$^{II}$(H$_2$O), $\Delta G_{11} > 0$ in water, since these metal aquo complexes are not acidic and N—OH can be expected to less stable than the N(H$_2$O) complexes.

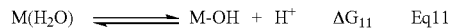

$$M(H_2O) \rightleftharpoons M\text{-}OH + H^+ \quad \Delta G_{11} \quad \text{Eq11}$$

As discussed above, for the case of Pt(II) and Hg(II) in acidic media, for effective catalysis with any species, that species must be present in significant concentrations. Thus, if catalysis is required with the less stable M-OH species in aqueous media, conditions must be adjusted to increase the concentration of this species. This is the role of the basic solvent, e.g. NaOH, in Eq 10 and is an aspect of the invention called solvent activation. By use of excess OH⁻, or using a solvent other than water, $\Delta G_{12}$ from Eq 12 would be expected to be more favorable than $\Delta G_{10}$ from Eq 10, $\Delta G_{12} < \Delta G_9$ and it is possible that with the appropriate set of conditions the equilibrium can favorable, $\Delta G_{12} \leq 0$.

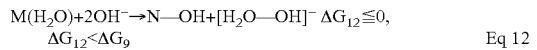

M(H$_2$O)+2OH⁻→N—OH+[H$_2$O—OH]⁻ $\Delta G_{12} \leq 0$,
$\Delta G_{12} < \Delta G_9$  Eq 12

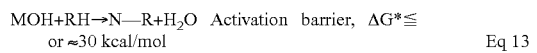

MOH+RH→N—R+H$_2$O Activation barrier, $\Delta G^* \leq$
or ≈30 kcal/mol  Eq 13

Figure 8:
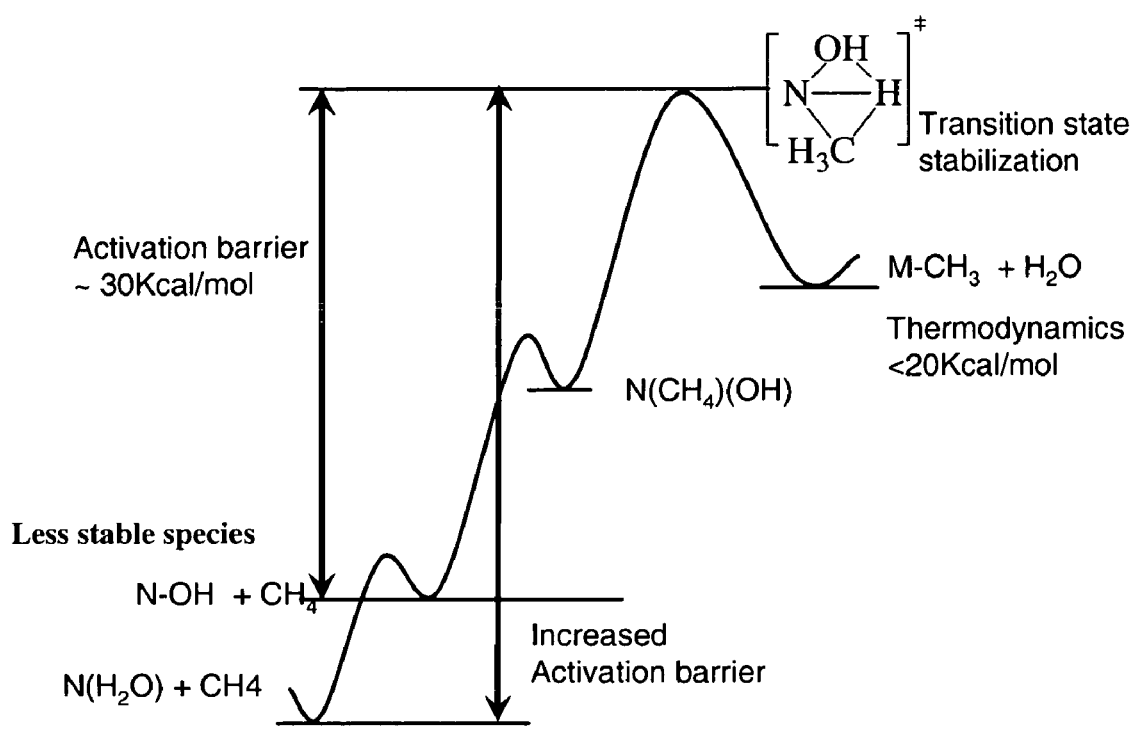
FIG. 8 is an energy diagram showing how the generation of less stable N—OH species can lead to activated catalysts.

Combining these concepts with the C—H activation reaction, Eq 13, an energy diagram, FIG. 8, can be drawn to illustrate the concept of using basic solvents to activate metals by the formation of less stable M-OH species toward reaction with hydrocarbons.

Figure 9:
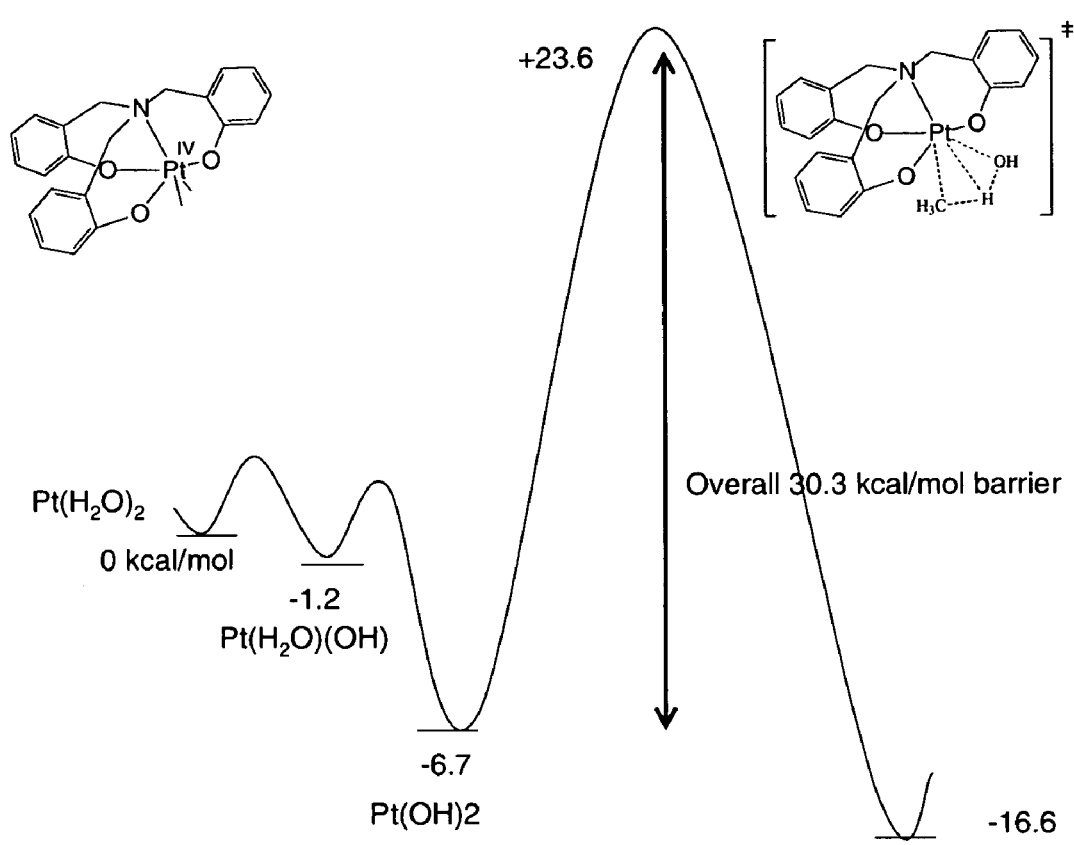
FIG. 9 is a calculated energy diagram for the reaction of (NOOO)Pt(IV) complex with methane.
Figure 10:
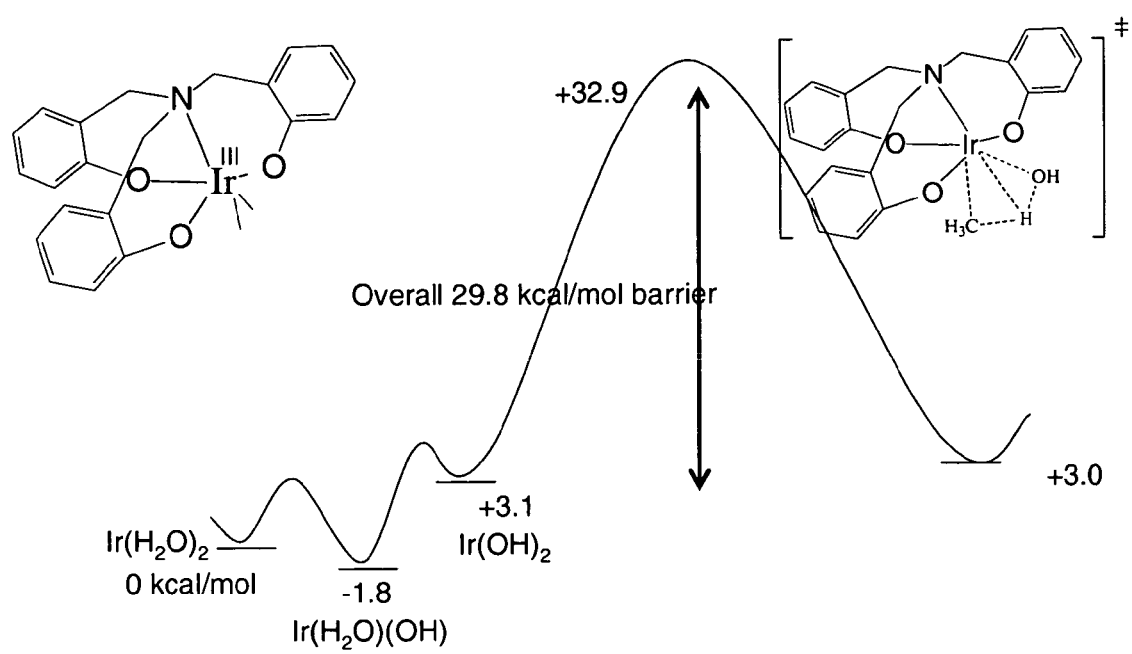
FIG. 10 is a calculated energy diagram for the reaction of (NOOO)Ir(III) complex with methane

Two examples that illustrate this concept on the basis of theoretical calculations are shown in FIG. 9 and FIG. 10. As can be seen, in the case of the tetradentate (NOOO)Pt(IV) complex the Pt(OH)$_2$ is lower in energy than the Pt(H$_2$O)(OH) complex which is lower in energy than the Pt(H$_2$O)$_2$ complex and it would be expected that base would inhibit reaction. However, in the case of Ir(III), a less electronegative metal, the formation Ir(OH)(H$_2$O) is slightly downhill but the formation of Ir(OH)$_2$ is uphill from the Ir(H$_2$O)$_2$ and strongly basis solution would be expected to accelerate reaction with alkanes.

Figure 11:
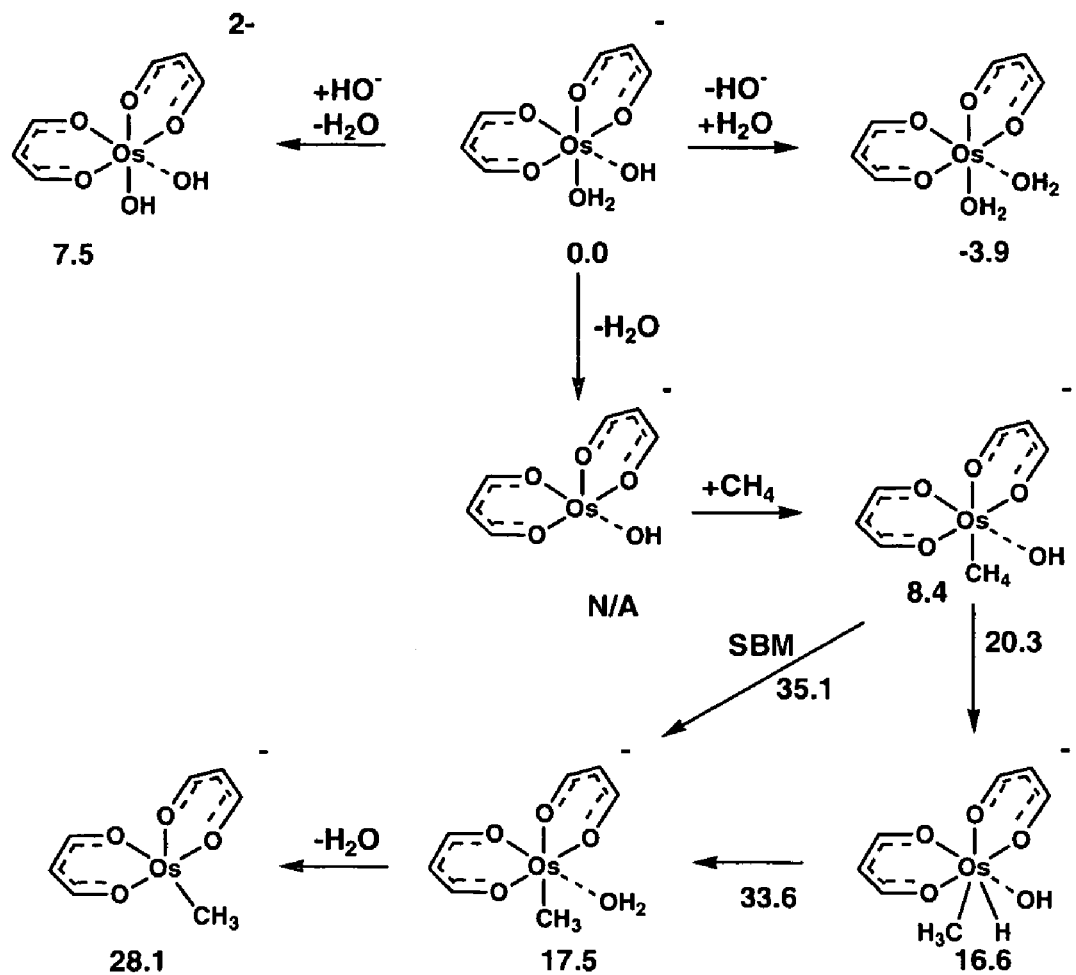
FIG. 11 shows a comparison of concerted (SBM) and a step-wise oxidative addition pathways one catalyst embodiment of the invention.

As depicted in FIG. 10, tetradentate (NOOO)Ir(III)(H$_2$O)$_2$ is less straight forward and requires further discussion to understand why the Ir(OH)(H$_2$O) is more stable than Ir(H$_2$O)$_2$ but Ir(OH)$_2$ is less stable. OH⁻ is a better sigma-donor than H$_2$O as seen by its affinity for a proton. Thus, initially the formation of OH is stabilizing. However, it is also a better π-donor and since Ir(III) is a $d^6$ metal with all of the d-orbitals of the $t_{2g}$ HOMO levels filled, increased filled-filled p-π to d-π repulsions between the d-π electrons on Ir(III) and the π-π electrons on OH could weaken the Ir$^{III}$—OH bond in the Ir(OH)$_2$ complex as discussed above. Consequently, depending on the LUMO level as well as the HOMO level of the electrons on the metal, (as well as the geometry sigma or pi, etc.) N—OH complexes can be expected to be more stable, comparable or even, with the appropriate choice of metals, less stable than the M-H$_2$O complexes. In FIG. 10, the transition state for C—H cleavage is a so-called Oxidative Hydrogen Migration or OHM. However, it is possible that other pathways involving oxidative addition to 7-coordinate (NOOO)Ir(OH)(H)(CH$_3$) intermediates, followed by water or OH⁻ assisted reductive elimination or Ir—H exchange could lead to more facile cleavage. The OHM (or Sigma Bond Metathesis, concerted reactions involving H transfer from C to OH) and Oxidative addition pathways are contrasted in FIG. 11. As can be seen from FIG. 11 the [(acac)$_2$Os(OH)$_2$]$^{2-}$ is ~10 kcal/mol above the (acac)$_2$Os(H$_2$O)$_2$ complex. Thus, starting from this complex to the generate the methane complex [(acac)$_2$Os(CH$_4$)(OH)]⁻ would reduce the barrier by 10 kcal/mol; this would lead to large improvements in rate. The key to generating the Os(OH)$_2$ is the hydration of OH⁻ with H$_2$O which can be worth ~10 kcal/mol of driving force.

Theoretical calculations can play an important role in facilitating the choice of appropriate metal catalyst. However, general predictions can also be made on the basis of known properties of metal and ligands. Thus, on moving to the left from Hg(II), that the HOMO and LUMO levels of metal ligand complexes would both increase in energy and the N—OH would be less stable than the N(H$_2$O)$_2$ and that such complexes would be activated in basic solution. Examples of such late transition metal hydroxides are Os$^{II}$—OH, Re$^I$—OH, Ir$^{III}$—OH. Oxidation state is important in so far as higher oxidation state metal hydroxides will be less basic and in fact can become acidic. Additionally, the nature of the ligands on the metal can also control the basicity or acidity of the metal hydroxides.

Dihydrogen molecule (H$_2$) is a good model of CH$_4$, albeit a more reactive model. This is because the homolytic bonds strengths are similar ~103 kcal/mol and radical reactions with CH$_4$ and H$_2$ require reactive intermediates or harsh conditions. Additionally, H-D exchange with H$_2$ or CH$_4$ is typically not observed in radical reactions. Consequently, if facile H-D exchange in observed with H₂ or CH₄ it is likely that reaction is occurring by H—H or C—H activation, not by a process which involves free radicals. To provide evidence for the use of basic solvents, the reaction of (acac-O,O)₂Os$^{IV}$Cl₂ in acidic and basic deuterated solvents with H₂ was studied. Contacting H₂ with (acac-O,O)₂Os$^{IV}$Cl₂ in acidic media (e.g. acetic acid or acidic water) showed no H-D exchange. However, on addition to the complex to basic water (10 wt % NaOH/D₂O), H₂ exchange was readily observed compared to the background reaction. [See Example 2]

Figure 12:
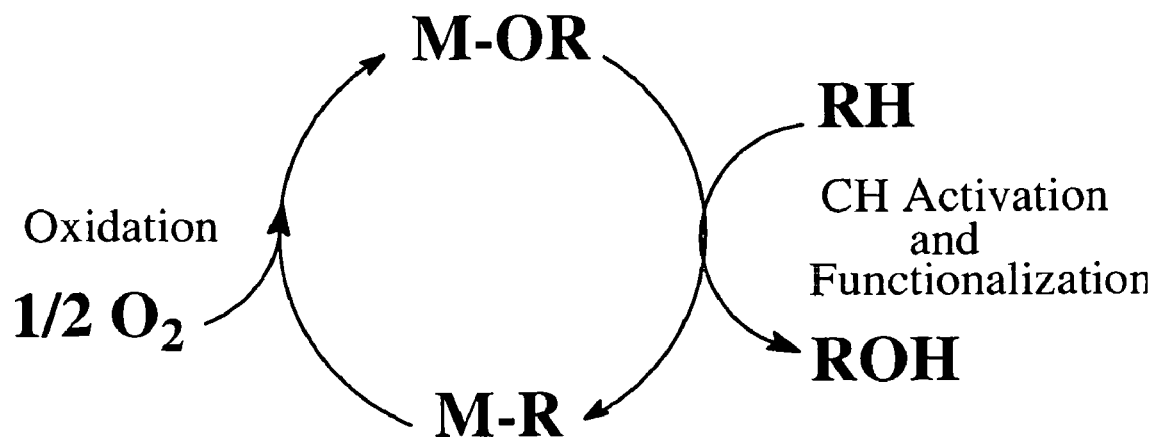
FIG. 12 shows a conceptual catalytic cycle for the conversion of hydrocarbons to alcohols that does not require a formal oxidation state change at the metal.

In addition to the C—H activation reaction, the metal ligand complexes of the present invention should allow catalytic cycles that provide the basis for developing of new, efficient catalyst systems that operate by Solvent Assisted Catalytic Oxidative Nucleophilic Substitution (SACONS). An example of such catalytic system which provides basis for processes according to the present invention is shown in FIG. 12. A key distinction in this catalytic cycle is that no formal redox changes at the metal center is required, with the reaction proceeding by insertion of an oxygen atom into the C—H activation intermediate, comprising a metal alkyl covalent bond, M-R.

Figure 13:
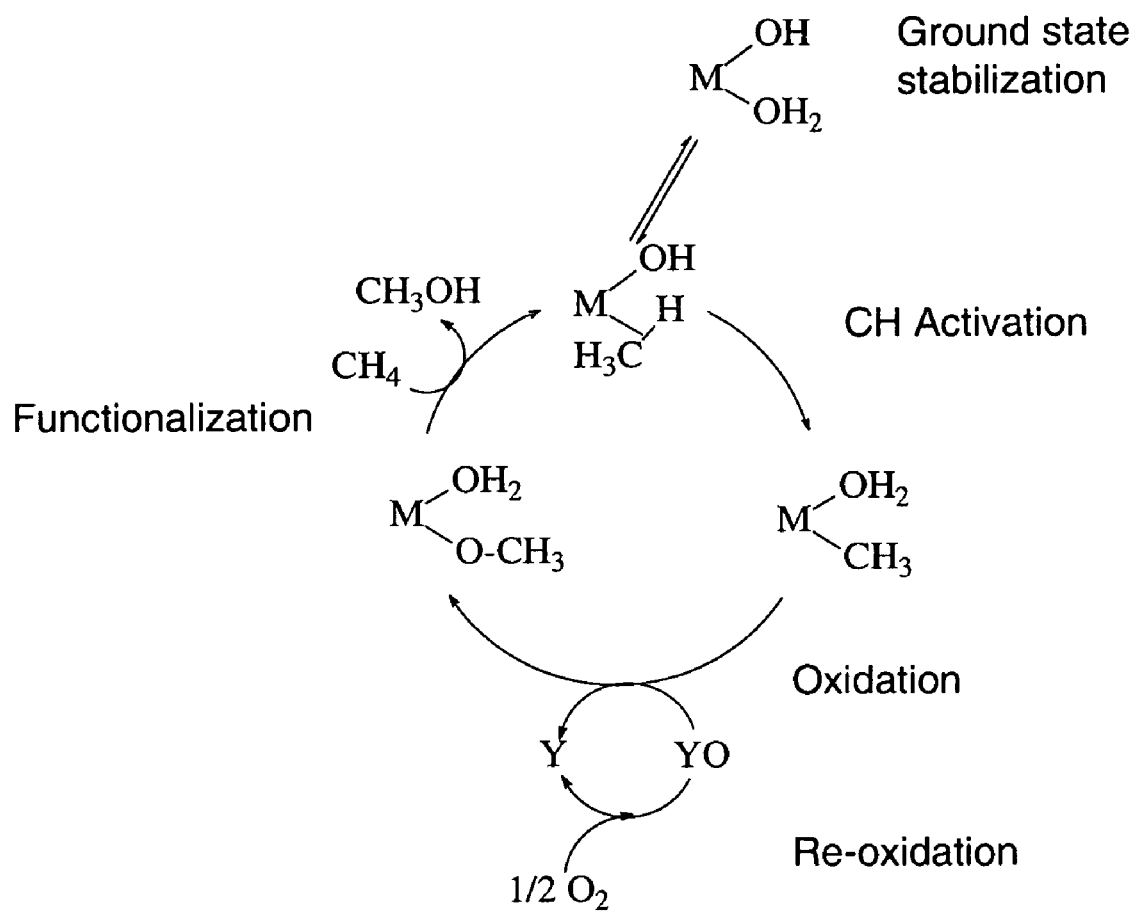
FIG. 13 shows a conceptual catalytic cycle for the conversion of hydrocarbons to alcohols based on the M-OH reaction.

The catalytic cycle shown in FIG. 12 involves the reaction of metal alkoxides, but an alternative allowed by catalyst systems of the present invention is shown in FIG. 13, which utilizes the conjugate base to the desired alcohol. Here metal-complexes which comprise hydroxyl ligands are used as shown in FIG. 13.

As shown in FIG. 13, the M-OR is converted to a M-OH species by reaction with water or other compatible solvents in a well precedented functionalization step.

Oxidation Step:

As shown in FIG. 12, the oxidation step is carried out directly with O₂. However, as shown in FIG. 13, the oxidation step can be carried out indirectly with an oxidant designated as YO. As shown, YO operates as a reversible O-atom donor/acceptor. This is a useful concept since YO can be used in recyclable, stoichiometric manner [as in the known Wacker process for the oxidation of ethylene to acetaldehyde with Cu(II)]. In practice these reactions are carried out in two reactors.

$$RH + YO \rightarrow ROH + Y \quad \text{Reactor 1} \qquad (Eq\ 14)$$

$$Y + \tfrac{1}{2}O_2 \rightarrow YO \quad \text{Reactor 2} \qquad (Eq\ 15)$$

$$\text{Net } RH + \tfrac{1}{2}O_2 \rightarrow ROH \qquad (Eq\ 16)$$

One advantage of the process in FIG. 14 is that O₂ is not mixed with the hydrocarbon during processing. This minimizes the formation of possible hydrocarbon/O₂ explosive mixtures, and minimizes loss of reaction selectivity due to free-radical reactions likely if the alcohol is generated in the present of reactions involving triplet ground state oxygen. The process also allows more flexibility of the design of M-R metal ligand complexes by alternative choices of YO, rather than being restricted to reaction with O₂.

Precedent for the conversion of M-R species into M-OR that is compatible with the generation of alcohols is known. It is known that RLi, R—Na, R₂Mg, etc. react with dioxygen, but these species are powerful bases and are not compatible with the generation of alcohols in basic solvent. More compatible with the generation of alcohols are reports that R—Ni reacts with O₂ to generate M-OR and alcohol by hydrolysis. However, it is likely that these reactions proceed via free-radical reactions, which would lead to other undesired products in addition to the desired alcohol. A closer precedent is the reaction of CH₃ReO₃ with H₂O₂ in basic solvent to generate MeOH and NaReO₄, Eq 17. This reaction proceeds relatively rapidly at room temperature in basic water containing hydrogen peroxide. The facility of this reaction suggests a low energy transitions state and a preferred pathway.

$$CH_3ReO_3 + H_2O_2 + NaOH \rightarrow CH_3OH + NaReO_4 + H_2O \qquad Eq\ 17$$

Figure 15:
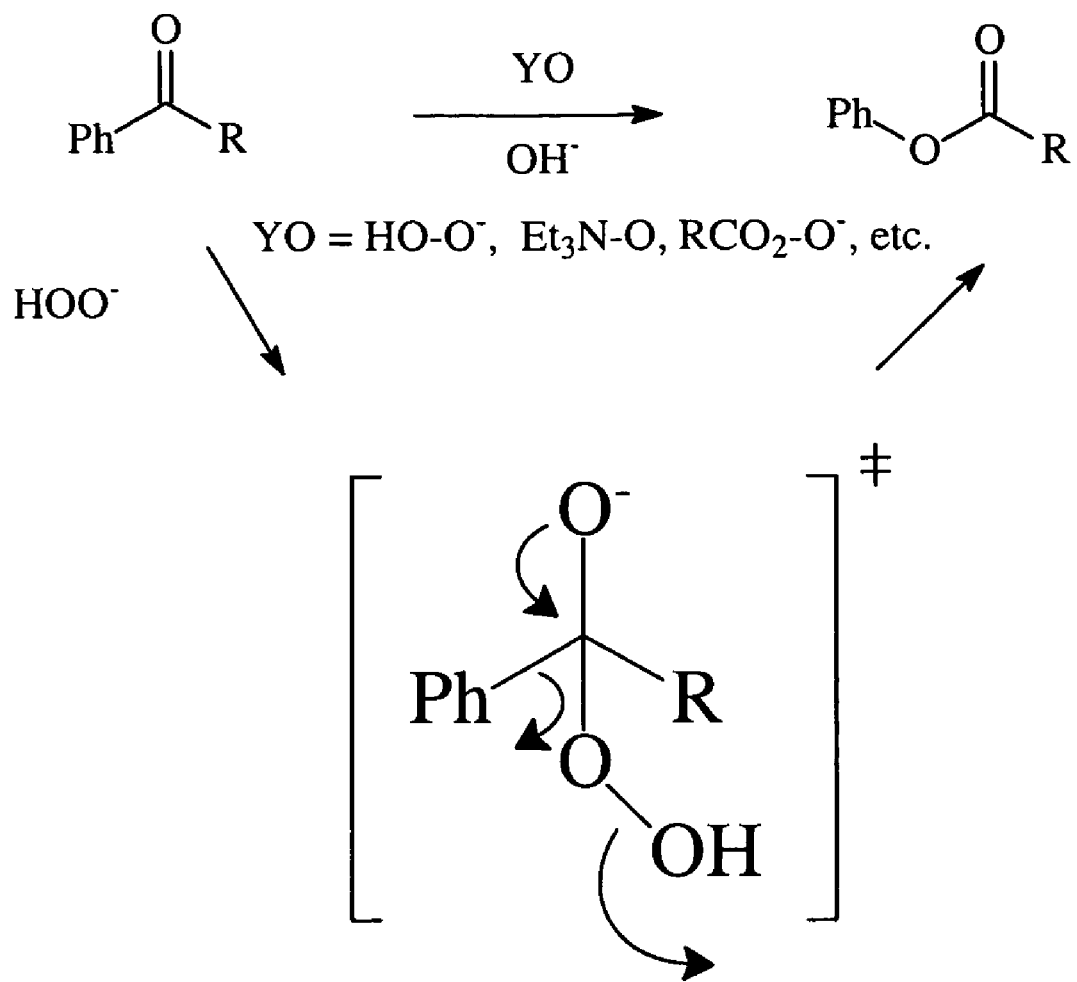
FIG. 15 shows a proposed reaction mechanism for the Baeyer-Villiger oxidation of phenyl ketones to phenyl esters with O-atom donor oxidants.
Figure 16:
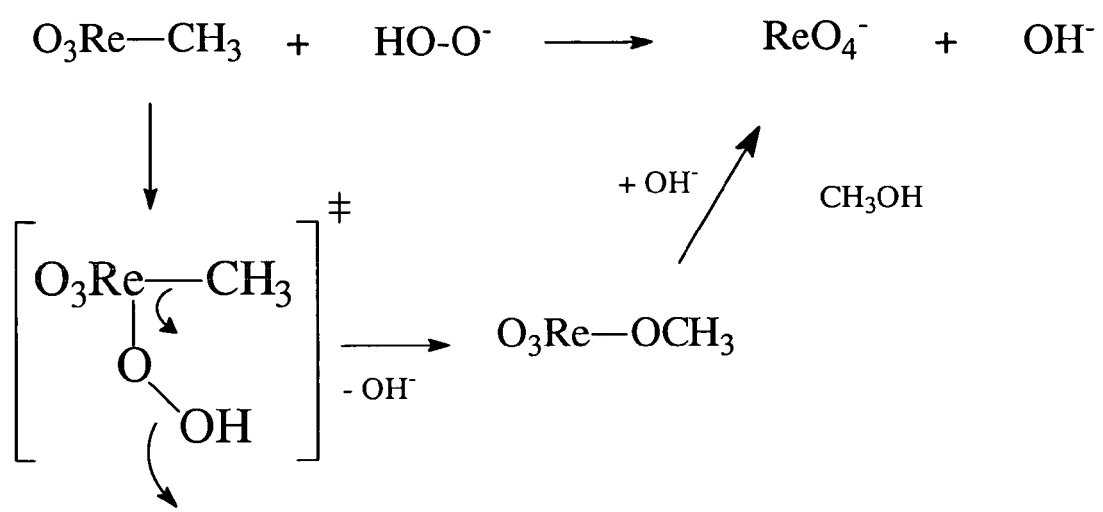
FIG. 16 shows a propose Baeyer-Villiger type mechanism for the oxidation of MTO to $CH_3OH$ via $CH_3OReO_3$.
Figure 17:
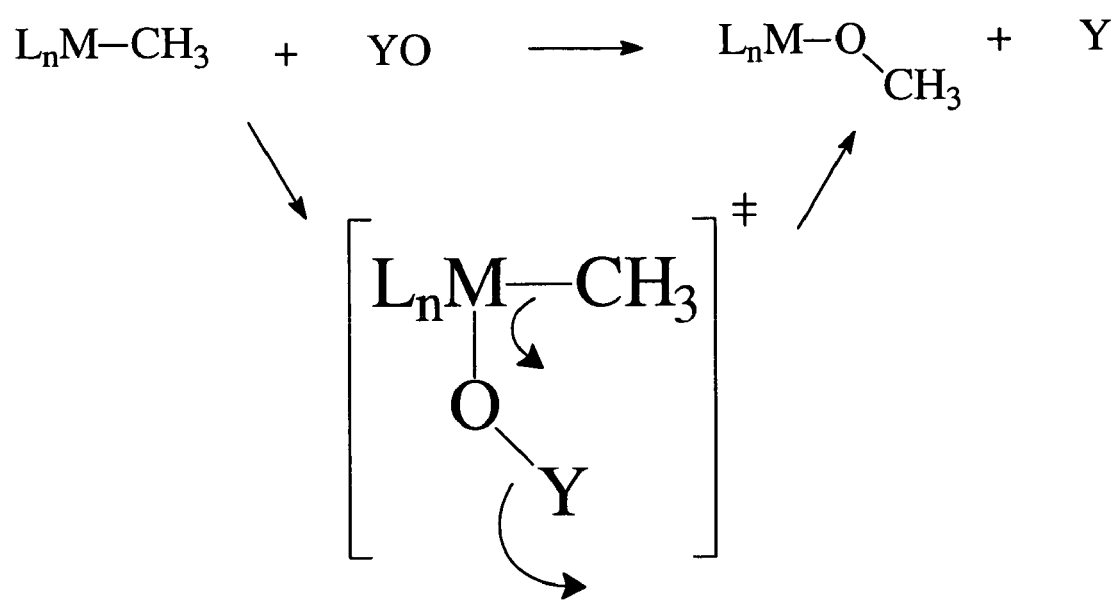
FIG. 17 shows a generalized scheme for the oxidation of M-R based on the Baeyer-Villiger and MTO oxidation mechanisms.

The reaction in Eq 17 was first reported by Espenson (Abu-Omar et al., J. Am. Chem. Soc 1996, 118, 4966-4974, and Espenson Chem Comm, 1999, 479-488) in the context of a process that destroys CH₃ReO₃ (MTO) since MTO is used in a variety of catalytic reactions. The focus of that work was not a method to generate methanol. Several mechanisms were proposed for the reaction. The reaction can be considered analogous to the facile Baeyer-Villiger oxidation of ketones, FIG. 15 that is used commercially. Analogous to the Baeyer-Villiger reaction we propose that the MTO reacts in a similar manner (FIG. 16). The comparison emphasizes that the OOH⁻ is an example of an O-atom donor, with OH⁻ as the leaving group, an acceptable leaving group in basic solution. This can be generalized as shown in FIG. 17 and can lead to the prediction of other oxidants for this reaction. FIG. 17 is a conceptual basis for several embodiments of the present invention.

Example Oxidants

The role of Y is as a leaving group and as a regenerable oxidant. In one embodiment of the invention, suitable YO oxidants are amine-N-oxide, cupric oxide, iron oxide, periodate ($IO_4^-$), vanadate ($VO_4^{3-}$), molybdate ($MoO_4^{2-}$), nitrous oxide ($N_2O$), hydrogen peroxide ($H_2O_2$), selenate ($SeO_4^{2-}$), tellurate ($TeO_4^{2-}$), hypochlorite ($ClO^-$), chlorite ($ClO_2^-$), nitrate ($NO_3^-$), and sulfoxides. Indeed, experiments found that several of these and related oxidants will convert MTO to methanol in basic water, confirming the generalized scheme shown in FIG. 17 (See Example 3 in the experimental section).

According to another embodiment of the invention, certain oxidants are regenerable with air or O₂. Suitable air or O₂ recyclable oxidants include but are not limited to cupric oxide (CuO), selenate, ($SeO_4^{2-}$), vanadate ($VO_4^{3-}$), and sulfoxide. Particularly useful examples of oxidants (YO) are those that can be reoxidized from Y to YO with oxygen or air. An example of such an oxidant is $SeO_4^{2-}$ as shown in FIG. 18.

The reactions of $SeO_4^{2-}$ with CH₄, catalyzed, e.g., by a catalyst of the present invention via the mechanism shown in FIG. 12 and FIG. 13, is favorable. Thus this reaction can be carried out in one reactor to yield methanol. In the second step or reactor, the regeneration of the reduced species, $SeO_3^{2-}$ an example of Y in FIG. 17, is also thermodynamically favorable and can be carried out with O₂ or air. Significantly, this reoxidation of $SeO_3^{2-}$ by O₂ to generate $SeO_4^{2-}$ is thermodynamically feasible only in basic solution. This shows an important advantage of the use of basic solvents; the reoxidation of many species become feasible. Other examples could be selected from CuO, FeO₂, $O_3VO^{2-}$, etc.

CH Bond Activation Examples:

Metal ligand complexes comprising M-OH or M-OR moieties react with hydrocarbons to generate M-R species by a C—H activation reaction. C—H bond activation is defined herein as a reaction that leads to the formation of a M-R species, without proceeding via the generation of free-radicals, carbocations or carbanions. Such C—H bond activation allows development of new catalysts that operate in basic media via the catalytic cycle shown in FIG. 12 and FIG. 13. Thus, as shown in the experimental results herein, the reaction of trans-(acac)₂Ir(OCH₃)(CH₃OH) with benzene leads to the trans-(acac)$_2$Ir(Ph)(L) complex as shown in Eq 15. This reaction was also found to be thermodynamically downhill using theoretical calculations and is consistent with the high reaction yield of ~75% based on added 2 in FIG. 4.

Given the expected similarities between M-OR and M-OH metal ligand complexes, this reaction in FIG. 4 provides precedent for the reactions shown in FIG. 12 and FIG. 13. The observation that metal ligand complex 2 in FIG. 4 dissolves in water to generate free methanol is consistent with the formation of the trans-(acac)$_2$Ir(OH)(H$_2$O) complex. This, coupled with the observation that an aqueous solution of 2 [or converted to trans-(acac)$_2$Ir(OH)(H$_2$O)] will catalyze exchange with benzene to provide a precedent for the reaction of M-OH species with hydrocarbons as shown in FIG. 12 and FIG. 13.

There is no requirement that a C—H activation reaction with M-OH or M-OR metal ligand complexes be thermodynamically downhill to be usefully incorporated into the catalytic cycles shown in FIG. 12 and FIG. 13. Indeed, assuming that an overall activation barrier of ~30 kcal/mol is acceptable for these catalytic reactions, catalysis is feasible even if the C—H activation step with either M-OH and M-OR metal ligand complexes with hydrocarbons to generate M-R intermediates is uphill by ~20 kcal/mol (assuming a ~10 kca/mol activation barrier for the reverse reaction).

Theoretical Example Section

Calculations have been carried out on several systems that show feasibility for C—H bond activation reactions with M-OH species. Two examples are shown on FIG. 27 and FIG. 28.

These calculations were carried out with highly accurate first principles quantum mechanics (QM) as described herein. This used Density Functional Theory (DFT) with hybrid exchange-correlation functionals based on the generalized gradient approximation (denoted as B3LYP). Numerous examples have now been published showing that these methods lead to very accurate kinetics (barrier heights) and reaction enthalpies in excellent agreement with experiment, where available. This establishes a level of confidence that the metal ligand complexes used in the calculations will lead to the rates and energetics close to those predicted. Such first principles bringing to practice of a newly invented catalysts has been used previously for zwitterion activated metathesis polymerization catalyst (Goddard III et al., U.S. Pat. No. 5,939,503) and polar olefin activation metathesis polymerization catalysts (Philipp et al., U.S. Pat. No. 6,777,510) both of which are incorporated herein by reference in their entirety.

Figure 19:
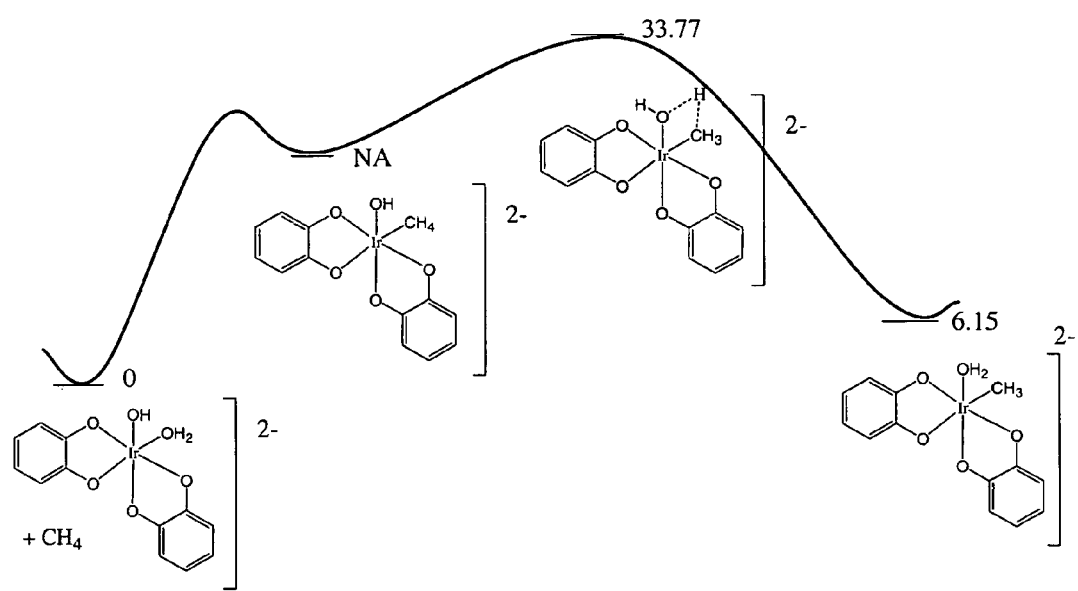
FIG. 19 shows a calculated barrier for the C—H activation with $(Cat)_2Ir$—OH species.
Figure 20:
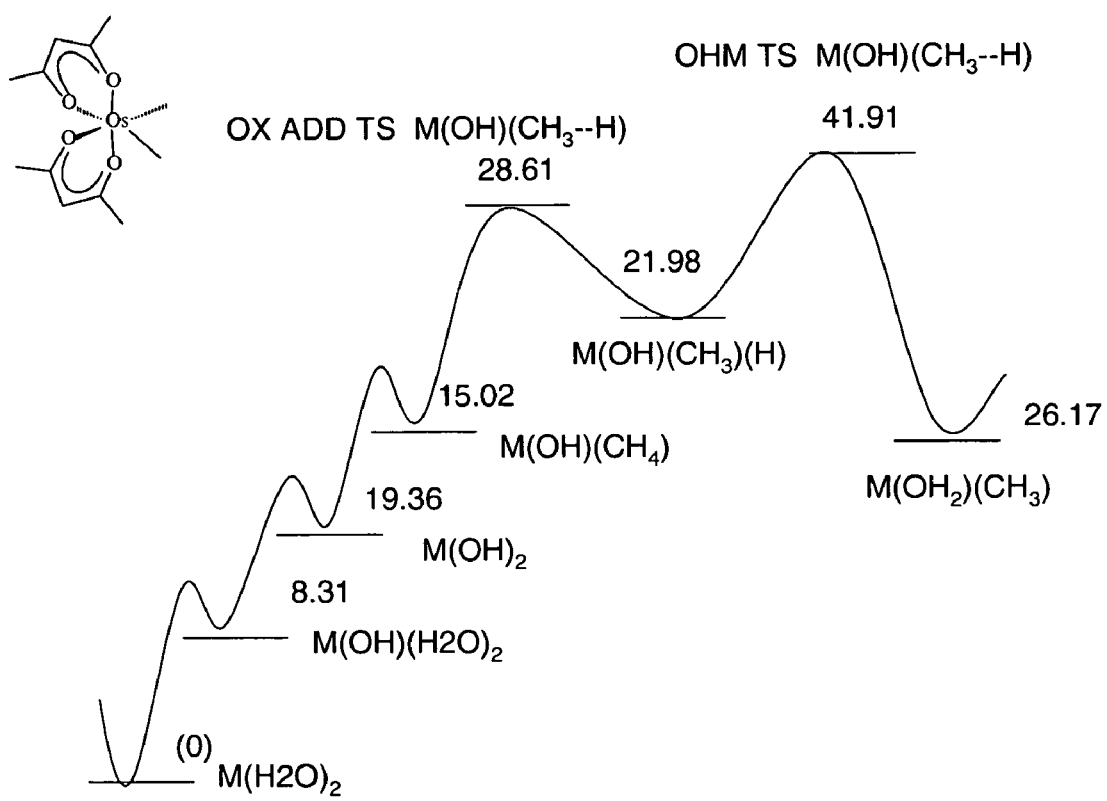
FIG. 20 shows a calculated barrier for the C—H activation with $(Cat)_2Os$—OH species.

Suitable d$^6$, 6-coordinate metal ligand complexes comprise four Group IV, Group V, or Group VI donor atoms as embodied within chelating ligands and two reactive sites occupied by labile solvent ligands such as aqueous $^-$OH and H$_2$O. Suitable ligand donor atoms can be O-donor atom ligands such as catechol and acetylacetonate as shown in FIG. 19 and FIG. 20 but other suitable ligands comprising Groups IV, V, and VI donor atoms include C, N, P, or S, and combinations thereof. Metal ligand complex can be designed to make the OH and H$_2$O groups cis to each other by chelating two, three, or all four ligands donor atoms as shown in FIG. 19 and FIG. 20.

A key challenge in the selective oxidation and conversion of alkanes to alcohols is that alcohols are more reactive than alkanes, especially in free-radical reactions such as the oxidation systems employed in other alkane conversion systems based on metal oxides. A key advantage of C—H activation based systems as embodied in the present invention is the avoidance of free-radicals in the reaction system and the observation that the alcohol product is less reactive than the alkane. Product protection was observed in the Hg(II), Pt(II) systems which operate in strongly acidic media but this product protection was attributed to the protonation or hydrogen bonding of solvent protons to the alcohol, [ROH—HX] which led to decreased electron density in the C—H bonds of the alcohol and decreased reactivity towards electrophillic metal ligand complexes.

Figure 25:
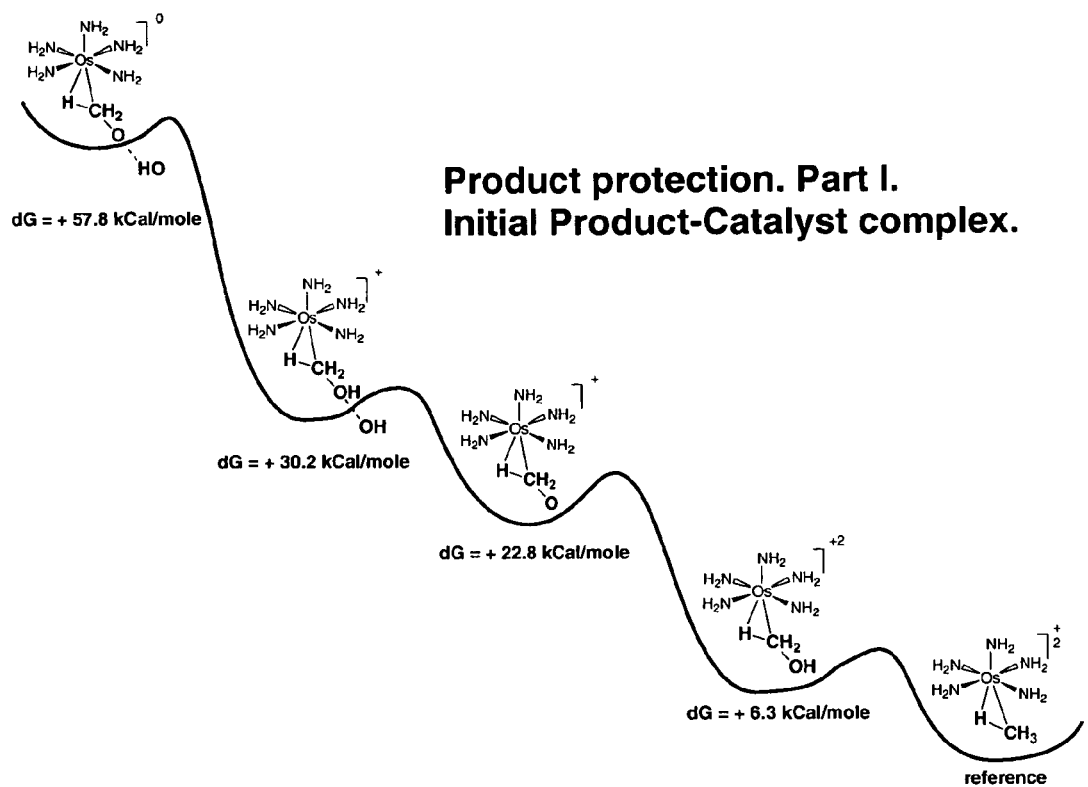
FIG. 25 depicts computational results showing that coordination of methanol and reaction with electron rich metal centers is expected to be inhibited by deprotonation or hydrogen bonding to $OH^-$.
Figure 26:
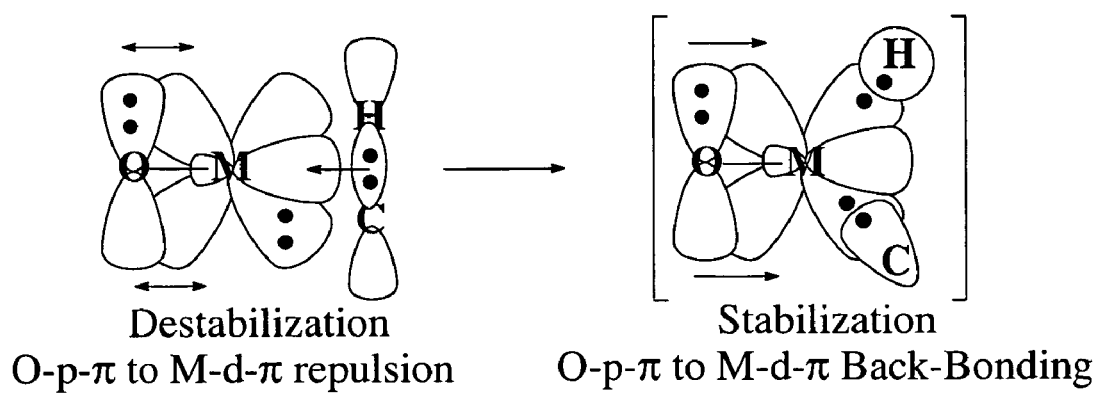
FIG. 26 shows a schematic illustration of π-donor involvement of the non-bonding electrons on o-donor ligands in C—H activation reactions with oxidative addition character.

In a similar manner, alcohol products in basic media are less reactive than alkanes towards nucleophilic metal catalysts as embodied in the present invention. This is because hydrogen bonding between the alcohols and the hydroxide, [ROH—OH]$^-$ increases the electron density on the C—H bonds of the alcohol since this effectively replaces a H—C—H bond with a H—C—O$^-$ bond. Since O$^-$ is more electron donating that H, the remaining C—H bonds in HCO$^-$ will be more electron rich and less reactive towards catalysts that interact primarily through metal HOMO to C—H LUMO interactions. This is shown by theoretical computations depicted in FIG. 25. Catalysts which operate via such electronic interaction (metal π-symmetry HOMO to alkane LUMO) may thus be called nucleophilic catalysts).

As a class, metal ligand complexes, comprising ligands which comprise O-donor atoms are experimentally observed to be kinetically labile. Transition metal ligand complexes which undergo rapid substitution of one ligand for another are labile, whereas complexes in which substitution proceed slowly or not at all are inert. Additionally, due to "hard soft" theoretical considerations, "hard" O-donor atom ligands are not compatible with "soft" late metals. Consequently, ligands comprising O-donor atoms are typically not employed in the design of soluble catalysts and the more kinetically inert ligands such as N, P, and C-donor ligands are more common. Importantly, this general observation of kinetic lability applies only to acidic, and especially strongly acidic media. Thus, while M-OCH$_3$ complexes are quite labile in acid media, these complexes can be kinetically inert and thus stable in basic media. Thus, for reactions in neutral or basis media, O-donor ligands are sufficiently stable spectator ligand to allow catalysis. While there are examples of O-donor atom, late metal complexes, the issue of incompatibility is most likely related to the challenges of synthesizing O-donor, late metal complexes because of the kinetic inertness of late metals.

Catalyst systems may be supported on metal oxides or other suitable supports. A key advantage of such supported catalysts is the high stability of the systems, due to the stability of the oxide support under oxidizing condition. Soluble, so-called "homogeneous" metal ligand complexes comprising O-donor atom ligands also exhibit some of the advantageous characteristics of heterogeneous systems.

Thus metal ligand complexes comprising oxidation resistant ligands which comprise ligating O-donor atoms exhibit greater oxidation stability. Suitable O-donor ligands include acetylacetonate (acac), tropolone, aryloxide, catechol, hydroxyacetophenone, e.g., 2-acetyl phenol metal ligand complexes. Compared to the N, C or P-donor ligands generally utilized for C—H activation, metal ligand complexes comprising O-donor atoms display higher thermal, protic and oxidant stability given the expected covalent character of oxygen-metal bonds with the late transition metals and the lower basicity of oxygen.

Another aspect of the present invention is that certain O-donor ligands result in significant changes in chemistry compared to complexes based on N, P and C-ligating atom ligands. Thus ligands comprising O-atom ligating atoms a) facilitate access to higher oxidation states, via hard/hard interactions or π-donation during catalysis that favor the functionalization step depicted in the generalized catalytic cycle [FIG. 2, FIG. 12, FIG. 13]; b) moderate the electron density, by the interplay of σ-withdrawing and π-donating properties at the metal center and reduce the possibility of the solvent, product or reactant inhibition that is generally observed with very electron-rich or electron-poor metal centers; and c) facilitate C—H bond activation reactions with electron-rich, late transition metal complexes that take place via "oxidative addition" or insertion pathways.

Theoretical and experimental evidence support has been presented for C—H bond activation reactions facilitated by π-donation through phenyl-Ir interactions. As O-donor ligands directly attached to a metal center can be efficient π-donors, it is likely that O-donor, $d^6$, 5-coordinate, square pyramidal metal ligand complexes benefit from ground state destabilization from non-bonding O-pπ to metal-dπ, filled-filled repulsions or so-called "π-conflict" as well as stabilization of the non-bonding O-pπ electrons by back bonding into empty metal-dπ orbitals when the M-C and M-H bond are formed by C—H activation, FIG. 27. 3-coordinate, $d^8$ and 5-coordinate $d^6$ metals are most suitable for these types of favorable π-π interactions. Specific metal ions redox pairs such as Pt(II)/IV), Ir(I)/(III), Os(II), Ru(II), Re(I) are suitable embodiments of C—H bond activating and functionalizing metal catalysts.

Figure 27:
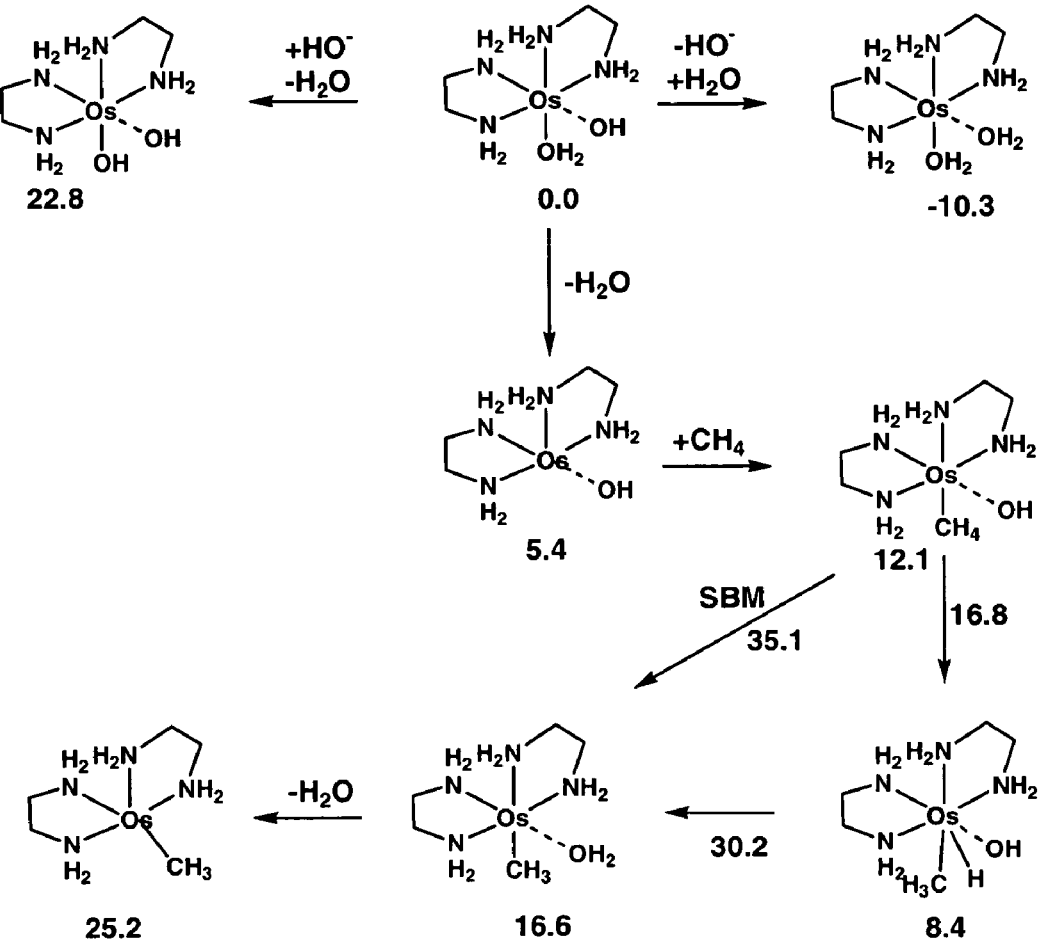
FIG. 27 shows a comparison of concerted (SBM) and a step-wise oxidative addition pathways one catalyst embodiment of the invention having ligating N atoms.
Figure 28:
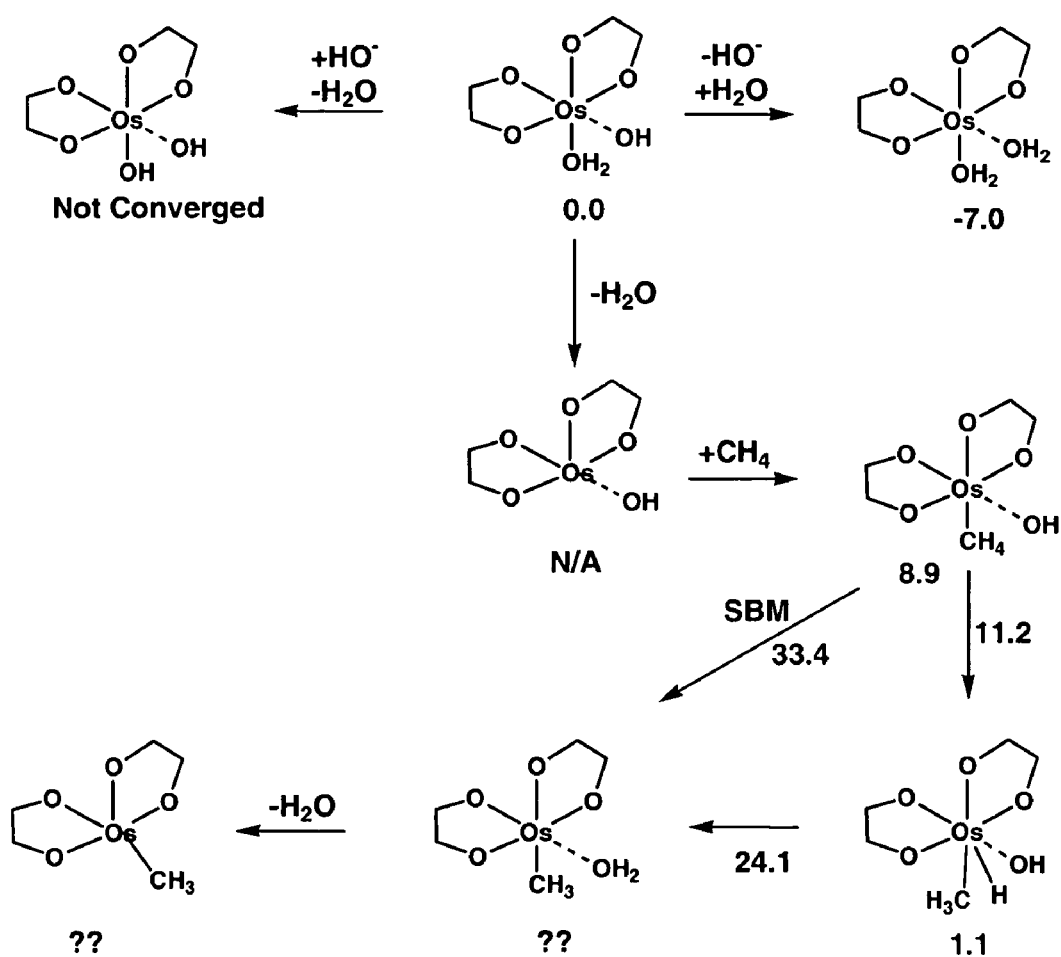
FIG. 28 shows a comparison of concerted (SBM) and a step-wise oxidative addition pathways one catalyst embodiment of the invention having ligating O atoms.

First principles QM calculations comparing related complexes with chelating N and O-donor atom ligands support the view that O-donor atom ligands are particularly suitable. Thus, as shown in FIG. 27 and FIG. 28, established supported by computations, the C—H activation reactions with Os(II) ethylene glycol and ethylene diamine complexes show that the O-donor ligated complexes exhibits lower barriers to C—H activation. As discussed earlier, the (acac-O,O)$_2$Ir(OMe)(MeOH) complex, an O-donor atom complex, exhibits facile reaction with arene C—H bonds and provides additional evidence that O-donor ligands can be effective for this reaction.

General bonding and electronic concepts supported by first principles theoretical calculations show that the reaction of low oxidation state, typically $d^6$ M-OH complexes of the third and second row metals that are not highly electronegative include good candidates for developing the catalytic cycles shown in FIG. 12 and FIG. 13. Specific metal ions redox pairs such as Pt(II)/IV), Ir(I)/(III), Os(II), Ru(II), Re(I) are suitable embodiments of C—H bond activating and functionalizing metal catalysts.

While suitable metal and metal ligand combinations have been identified, a remaining issue is whether such low oxidation state metals can be used in the presence of oxidants, such as O-atom donors, abbreviated as YO. This is a general issue for catalytic systems to carry out oxidation reactions in which the desired oxidation state of the catalyst is lower than the highest oxidation state possible for the metal used as the catalyst. The issue is that the low oxidation state metal ligand complex, $M^n$-OH can (in addition to reacting with the hydrocarbon C—H bonds in the C—H activation reaction) in the presence of the oxidant YO (which is required for the net oxidation reaction to be present in relatively high concentration) be oxidized to higher oxidations state metal ligand complex, $M^{n+2}$-OH that can be less reactive with the alkane as shown in FIG. 21.

Figure 21:
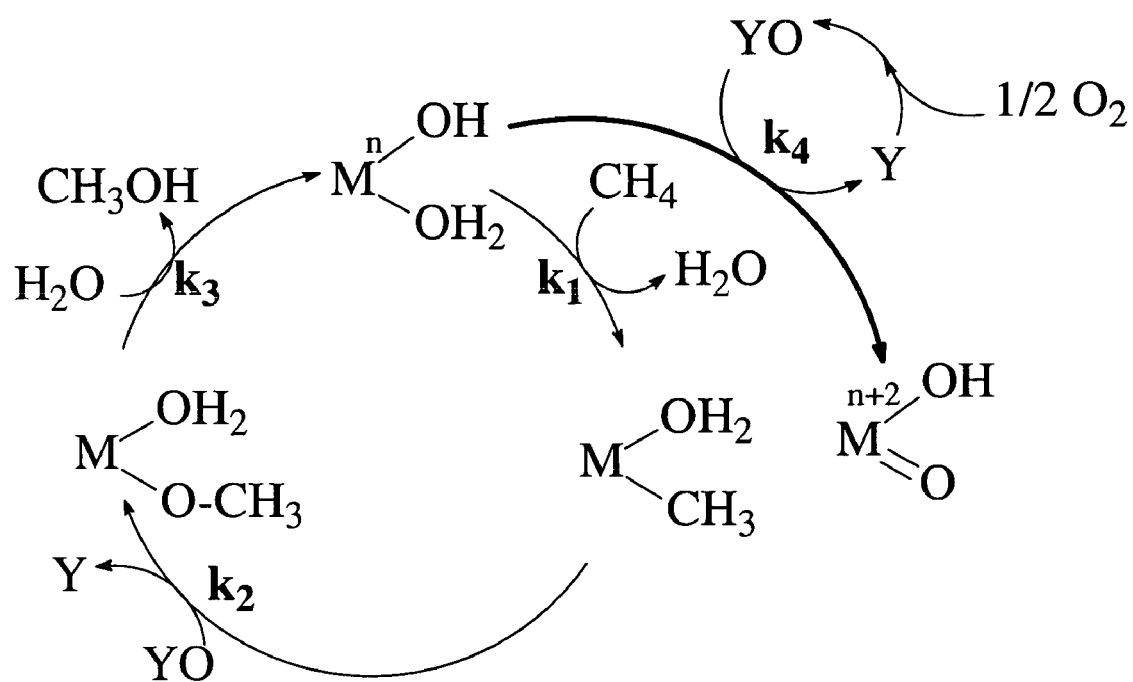
FIG. 21 shows a conceptual cycle for the oxidation of $CH_4$ with low oxidation state catalyst, $M''(OH)(H_2O)$, with the competing oxidation by YO.

One issue illustrated in FIG. 21, is that if step $k_4$ occurs to produce irreversibly a higher oxidations state metal ligand complex, $M^{n+2}(=O)(OH)$, that does not react with alkane, $CH_4$ [or reacts slower than $M^n(OH)(H_2O)$] the desired catalytic cycle will inevitably stop (drop to some impractical rate that can be defined as 1/10 of the desired catalytic rate) in some number of catalytic cycles depending on the relative rates of step $k_4$ ($k_4[M^n(OH)(H_2O)][YO]$) to that of the overall desired catalytic cycle. This is because most if not all of the metal ligand complex would eventually exist as $M^{n+2}(=O)(OH)$ so that catalysis effectively stops. If we assume that $k_1$ is the rate limiting step in the catalytic cycle, the rate of the catalytic cycle will be given by $k_1[CH_4][M^n(OH)(H_2O)]$ and the number of cycles before catalysis effectively stops will be related to the $k_1[CH_4]/k_4[YO]$. Thus, if $k_4$ is larger than $k_1$ and the concentration of YO greater than $CH_4$, then the catalysis can stop quickly or indeed never be observed.

Figure 22:
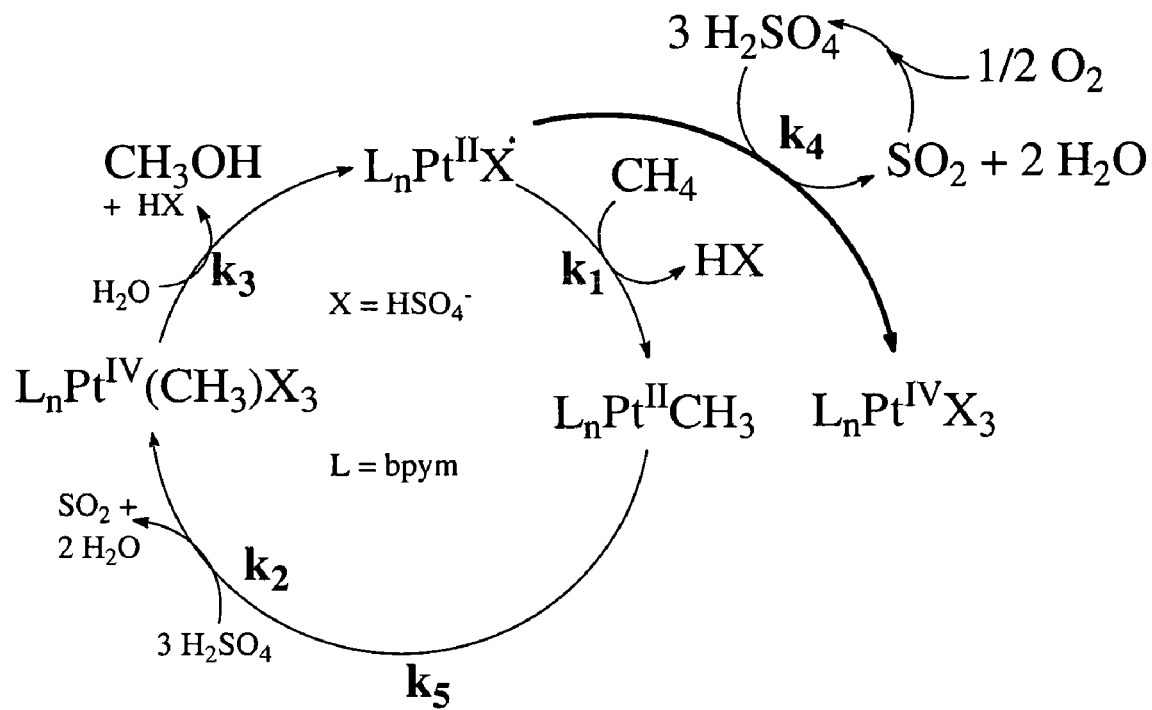
FIG. 22 shows a catalytic cycle for the $Pt(bpym)Cl_2/H_2SO_4$ system showing the issue with oxidation of the active Pt(II) catalyst with $H_2SO_4$ to generate inactive Pt(IV).

This situation can exist in all oxidation systems for which the desired catalyst is a lower oxidation state species. Thus, in the Pt(bpym)Cl$_2$ system in strong acid, this situation also exists because in this system the preferred oxidation state for the catalyst to react with methane (which can be the rate determining step) is Pt(II) and not Pt(IV). This is shown in FIG. 22. The reactions rates of Pt(IV) with methane are substantially lower.

This raises the key question of designing catalyst systems such that they will not be deactivated by such a process. Such a design is possible in general and can be understood by examining the Pt(bpym)Cl$_2$ system in strong acid which is a viable catalyst system in strong acid in spite of the observation that step $k_4$ does take place.

Figure 23:
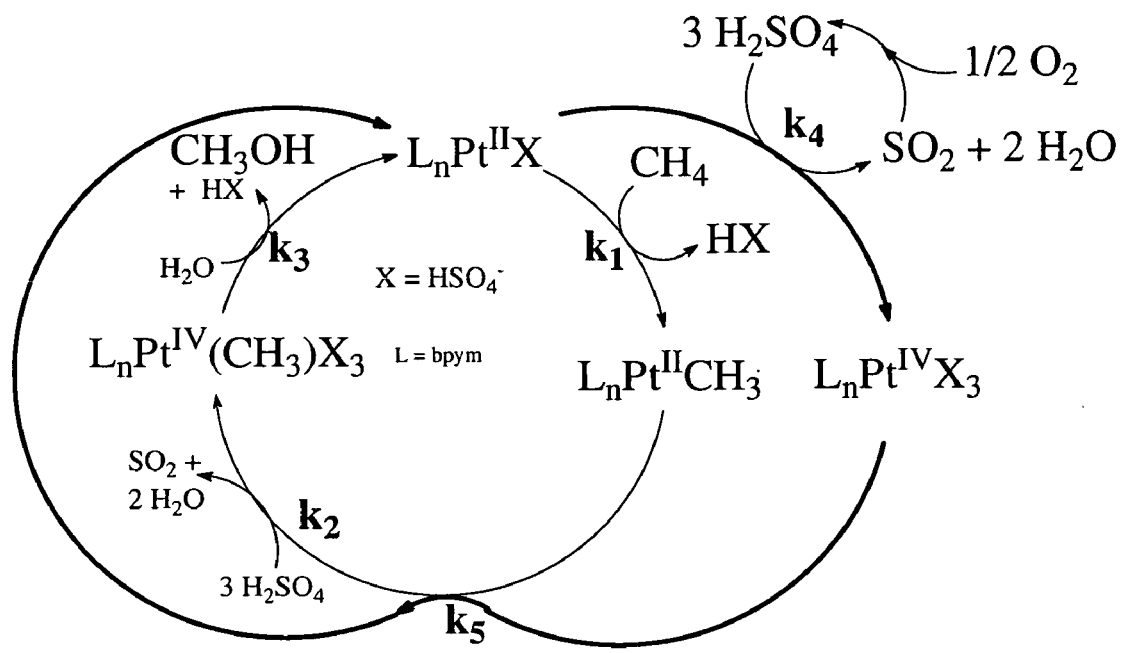
FIG. 23 shows a catalytic cycle showing why the Pt(bpym)$Cl_2$ is Stable in Lieu of the oxidation of active Pt(II) catalyst to Pt(IV).

One design strategy is to attempt to make $k_4$ much slower than $k_1$. i.e. slow down the irreversible oxidation of the catalyst. However, this is impractical since oxidation is required in the catalytic cycle of the Pt(bpym)Cl$_2$ system. Indeed even if possible this will only slow but not prevent the death of the catalyst. One aspect of the present invention is to design a stable catalyst system is recognizing that there are pathways for the reaction of the high oxidation state of the catalyst [the $L_nPt^{IV}X_3$ species produced in $k_4$] that will regenerate the active catalyst, $L_nPt^{II}X$. Such a step is shown in FIG. 23 as $k_5$. Thus, it is known that L*Pt(IV) species readily react with LPt(II) species to degenerately produce L*Pt(II) and LPt(IV) species by atom-transfer reactions, even when L and L* are the same species. In reaction, $k_5$, this reaction of $LPt^{IV}X_3$ with $LPt^{II}(CH_3)$ has been shown to be both facile and thermodynamically possible because both $LPt^{IV}(CH_3)X_3$ and $LPt^{II}X$ are more stable than the reactants, Eq 18. This is because $CH_3$ is more electron donating that X ($HSO_4^-$) and will stabilize Pt(IV) more than Pt(II) and is likely the major driving force of Eq 18 that makes the reaction favorable. Additionally, $X^-$ may stabilize Pt(II) more than Pt(IV) but this is most likely not the major driver of the reaction.

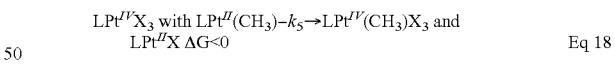

$$LPt^{IV}X_3 \text{ with } LPt^{II}(CH_3) - k_5 \rightarrow LPt^{IV}(CH_3)X_3 \text{ and } LPt^{II}X \; \Delta G<0 \qquad \text{Eq 18}$$

Thus, the Pt(bpym)Cl$_2$ system is stable because the active catalyst, $LPt^{II}X$ is not irreversibly converted to inactive $LPt^{IV}X_3$ because of the facile nature of step $k_5$. Note that step $k_5$ makes the system auto catalytic towards a steady state system, because forming any $LPt^{II}CH_3$ facilitates the generation of the active catalyst, $LPt^{II}X$ by reduction of the inactive form, $LPt^{IV}X_3$. This in turn leads to the formation of more $LPt^{II}CH_3$. Consequently, if step $k_5$ is competitive with the other catalytic steps, the system will reach steady state conditions where the catalyst will speciate between all the states shown in FIG. 23, rather than eventually all going to $LPt^{IV}X_3$ which would stop the catalysis.

Figure 24:
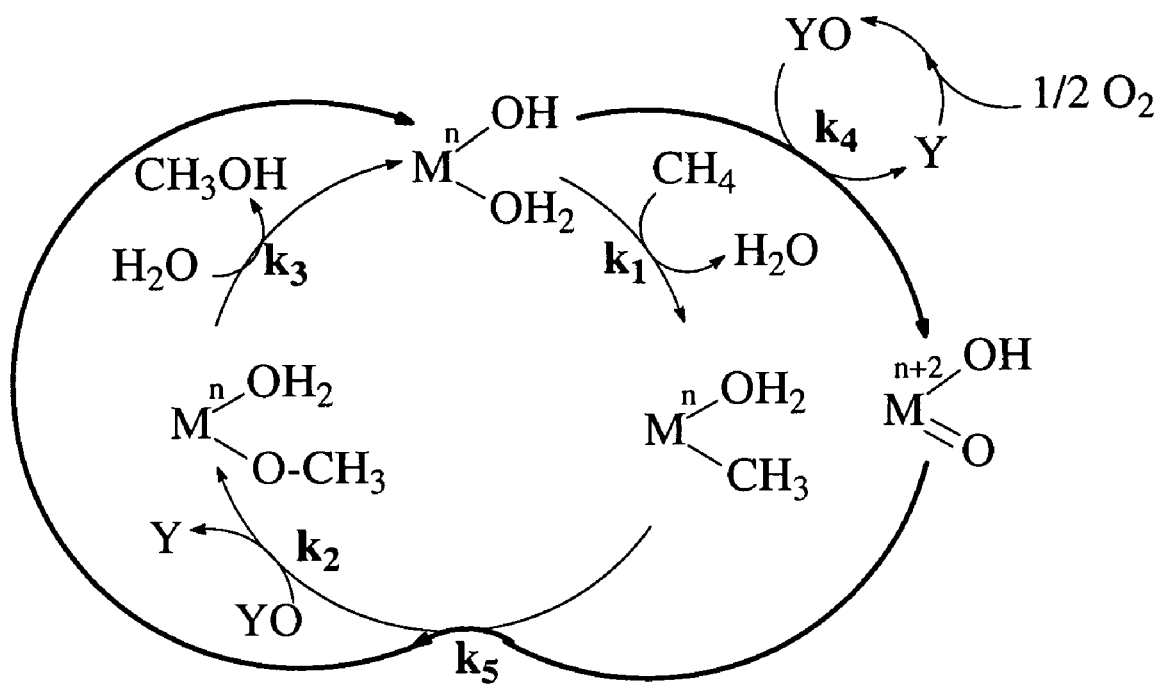
FIG. 24 shows a catalytic system showing the introduction of the $k_5$ step that prevents catalyst deactivation from irreversible oxidation.

Insight into the Pt(bpym)Cl$_2$ system in strong acid suggests a general way of preventing low oxidation state catalysts from becoming deactivated from irreversible oxidation to inactive, high oxidation states in oxidation reactions. In the case of catalyst systems that operate by the catalytic cycles shown in FIG. 21, the general solution is to design a catalyst system to allow the $k_5$ step shown in FIG. 24 to operate.

As in the case of the Pt(bpym)Cl$_2$ system in strong acids, the key is to ensure that the inactive, higher oxidation state of the catalyst, $M^{n+2}$(=O)(OH), can react in step $k_5$ to regenerate the active catalyst $M''$(OH)(H$_2$O) in the process of oxidizing the catalytic species, $M''$(CH$_3$)(H$_2$O) to the $M''$(OCH$_3$) (H$_2$O). This can be expected to be a favorable reaction if $M^{n+2}$(=O)(OH) is and $M''$(OCH$_3$)(H$_2$O) are of comparable stabilities and is facilitated by the presence of the CH$_3$ electron donating group. A key to facilitating this reaction in basic media is to utilize metal ligand complex with similar stabilities between consecutive oxidation states. Examples of such metals are Re, Os, Ir, Ru, W, and Rh. These metals are in the middle of the transition series of the periodic table where the differences in consecutive ionizations energies are among the smallest.

Experimental and Computational Section

The calculated reaction pathways and energetics shown in FIGS. 9-11, 19, 20, 25, 27, and 28 were determined using first principles quantum mechanics (QM) using the B3LYP flavor of Density Functional Theory (DFT). This DFT functional utilizes the Becke three-parameter hybrid functional (Becke, A. D. *J. Chem. Phys.* 1993, 98, 5648) combined with the correlation functional of Lee, Yang, and Parr (Lee et al., *Phys. Rev. B* 1988, 37, 785.), as implemented in the Jaguar 5.5 and 6.0 software packages (Jaguar 5.5, Schrodinger, Inc., Portland, Oreg., 2000; Jaguar 6.0, Schrodinger, Inc., Portland, Oreg., 2005). B3LYP is has been established to produce accurate descriptions of reaction profiles for transition metal containing compounds (see Baker et al. *In Chemical Applications of Density-Functional Theory*; Laird, B. B., Ross, R. B., Ziegler, T., Eds.; ACS Symposium Series 629; American Chemical Society: Washington, D.C., 1996, and Niu et al., *Chem. Rev.* 2000, 100, 353). The metals were described by the Wadt and Hay core-valence (relativistic) effective core potential (treating the valence electrons explicitly) using the LACVP basis set with the valence double-ζ contraction of the basis functions, LACVP** (see Hay & Wadt *J. Chem. Phys.* 1985, 82, 299; Goddard III *Phys. Rev.* 1968, 174, 659; and Melius et al., *Chem. Phys. Lett.* 1974, 28, 457). For all other elements (H, C, O, N) all electrons were described explicitly using a modified variant of the Pople 6-31G** basis set, where the six d functions are reduced to five (see Hariharan & Pople *Chem. Phys. Lett.* 1972, 16, 217 and Francl et al., *J. Chem. Phys.* 1982, 77, 3654).

It is important in obtaining the energetics and reaction pathways to include the effects of the polarization of the solvent on the structures and energetics, especially the barrier heights for the transition states. To carry out such calculations, the Poisson-Boltzmann (PBF) continuum method (see Tannor et al., *J. Am. Chem. Soc.* 1994, 116, 11875, and Marten et al., *J. Phys. Chem.* 1996, 100, 11775) was used which accounts for the polarization of the solvent due to the electrostatic field from the QM description of the molecular complex. The PBF method is a polarizable Self Consistent Reaction Field method with its energy calculated self-consistently to include the reaction of the solvent polarization field on the electrons and structure of the molecular complex. The PBF implementation in the Jaguar 5.5 and 6.0 software packages, which has been established to yield excellent values was used. For calculation in water, the aqueous environment ($\epsilon$=80.37 and probe radius=1.40 Å) was used. The standard set of van der Waals radii as defined in Jaguar, for example, H (1.150 Å), C (1.900 Å), 0 (1.600 Å), Cl (1.974 Å), Br (2.095 Å), Pd (1.450 Å), and Pt (1.377 Å) were used.

Due to the increased cost of optimizing systems in the solvated phase (increase in computation time by a factor of ~4) the solvation effects reported are sometimes calculated as single point solvation corrections to gas phase geometries. Work on the Ir(acac)$_2$ system showed that the total energies, geometries, frequencies and zero point energies were largely unchanged when the systems were optimized in the solvation phase.

Energies in FIGS. 9-11, 19, 20, 25, 27 are reported as $\Delta H(0K)=\Delta E+$zero point energy correction+solvation correction. Relative energies on the $\Delta H(0K)$ surface are expected to be accurate to within 3 kcal/mol for stable intermediates, and within 5 kcal/mol for transition structures (see Bhalla et al., *J. Am. Chem. Soc.*, 2005, 127, 11372). Moreover, relative energies of iso-electronic species (such as regio-isomers) are considerably more accurate, since the errors largely cancel.

Free energies were calculated as $\Delta G(473K)=\Delta H(473K)-T\Delta S(473K)$, where $\Delta H=\Delta E$(gas phase)+$\Delta E$(solvation correction)+ZPE+$\Delta H$(vib)+$3kT^*\Delta(n)$. The last term, 3kT, is a fixed value for the sum of the rotational and translational contributions to the enthalpy at 473K, calculated to 2.823944 kcal/mol. $\Delta S$ terms were calculated by summing up the $\Delta S$(vib)+$\Delta S$(trans/rot)+$\Delta S$(conc). $\Delta S$(vib) is taken from the Jaguar gas phase calculation at 473K, while $\Delta S$(trans/rot) is given a fixed value of 30 cal/mol*K.

The use of 3kT and 30 cal/mol*K for the $\Delta H$(trans/rot) and $\Delta S$(trans/rot) terms, respectively, was made to account for the reduced values of a solvent from the values obtained in gas-phase calculations of thermodynamic properties. For a solvated reaction these gas-phase values are substantially smaller (see Truong et al., *J. Chem. Phys.* 1997, 107, 1881, and Cramer & Truhlar *Chem. Rev.*, 1999, 99, 2161).

All geometries were optimized and evaluated for the correct number of imaginary frequencies through vibrational frequency calculations using the analytic Hessian. Zero imaginary frequencies correspond to a local minimum, while one imaginary frequency corresponds to a transition structure. Although the singlet states are expected to be the lowest energy spin states, we also investigated higher spin states for select geometries, and invariably found the singlet as the lowest energy state.

To reduce computational time the methyl groups on the acac ligands were replaced with hydrogens. Control calculations show that relative energies of intermediates and transition structures change less than 0.1 kcal/mol when methyl groups are included.

All air and water sensitive procedures were carried out either in a MBraun inert atmosphere glove box, or using standard Schlenk techniques under argon. Methanol was dried from Mg/I$_2$, and benzene from sodium/benzophenone ketal. All deuterated solvents (Cambridge Isotopes), and NaOCH$_3$ (Aldrich) were used as received. Complexes 1 and 1-Cl were prepared as described in the literature (Matsumoto et al., *J. Mol. Cat. A-Chemical* 2002, 180, 1). GC/MS analysis was performed on a Shimadzu GC-MS QP5000 (ver. 2) equipped with cross-linked methyl silicone gum capillary column (DB5). The retention times of the products were confirmed by comparison to authentic samples. NMR spectra were obtained on a Varian Mercury-400 spectrometer at room temperature. All chemical shifts are reported in units of ppm and referenced to the residual protonated solvent. All high-resolution mass spectra were obtained by UCLA Pasarow Mass Spectrometry Laboratory on an ESI mass spectrometer. Elemental Analysis was performed by Desert Analytics of Tucson, Ariz.

Synthesis of [CH$_3$O—Ir(O,O-acac)$_2$(CH$_3$OH)] (2-CH$_3$OH): To a 30 mL thick-walled ampoule equipped with a high-vacuum valve at top [acac-Ir(O,O-acac)$_2$]$_2$ 1 (370 mg, 0.38 mmol), sodium methoxide (128 mg, 2.37 mmol), and 30 mL methanol were added. The mixture was heated at 130° C. with stirring for 30 min. During this time the color of the solution turned from yellow to dark red. After cooling, the solution was twice filtered through a pad of basic alumina on a medium porosity frit, and purified by centrifugal thin layer chromatography using ethyl acetate: methanol 9:1 on alumina (the material was loaded onto the disk using methylene chloride and washed with methylene chloride for approximately 5 minutes before eluting. The eluent was concentrated under vacuum to yield approximately 74 mg (22%) of title complex as an orange solid. $^1$H NMR (CD$_3$OD): δ 5.50 (s, 2H, CH), 2.83 (s, 3H, Ir—OCH$_3$), 2.01 (s, 12H, CH$_3$). $^{13}$C{$^1$H} NMR (CD$_3$OD): δ 187.39 (C-acac, C=O), 103.9 (O-acac, CH), 55.9 (OCH$_3$), 27.0 (O-acac, CH$_3$). HRMS (ESI): Calculated for C$_{12}$H$_{22}$IrO$_6$ (M+H) 455.1046. found 455.1035. Elemental Analysis: Calculated for C$_{12}$H$_{21}$IrO$_6$: C, 31.78; H, 4.67. Found: C, 31.82; H, 4.53. Single crystals were grown by slow evaporation of a concentrated sample in chloroform.

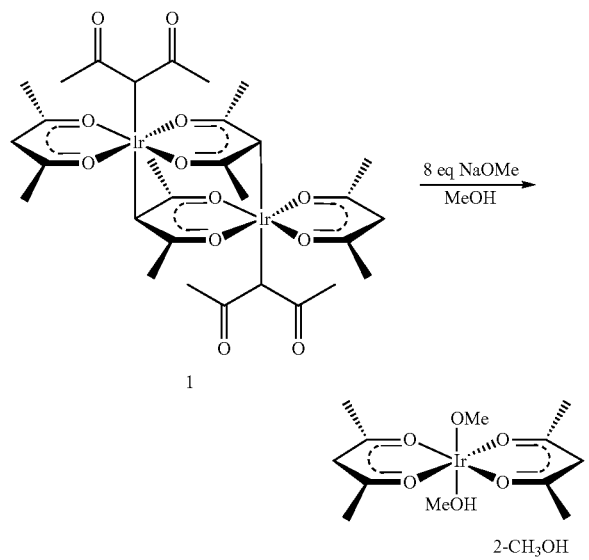

Alternative synthesis of [CH$_3$O—Ir(O,O-acac)$_2$(CH$_3$OH)] (2): To a 50 mL re-sealable Schlenk tube [Cl—Ir(O,O-acac)$_2$]$_2$ 1-Cl (250 mg, 0.29 mmol), sodium methoxide (125 mg, 2.32 mmol), and 30 mL methanol were added. The mixture was heated to gentle reflux with stirring for 32 hr. During this time the color of the solution turned from yellow to dark red. The volatiles were removed from the tube under vacuum, and the remaining solids were dissolved in methylene chloride, filtered through a medium porosity frit, and purified by column chromatography using ethyl acetate: methanol 5:1 on alumina. The eluent was concentrated under vacuum to yield 5% of title complex as an orange solid.

Synthesis of [CH$_3$O—Ir(O,O-acac)$_2$(Py)] (2-Py): A 15 mL re-sealable Schlenk tube was charged with 2-CH$_3$OH (10 mg, 0.022 mmol) and pyridine (7 mL) was added. The Schlenk tube was then sealed, and placed in a 55° C. oil bath for 30 min. The resulting yellow-orange solution was cooled to room temperature, and the volatiles were removed under vacuum, yielding a yellow-orange solid in quantitative yield. The product was recrystallized from dichloromethane. $^1$H NMR (CDCl$_3$): δ 8.25 (d, 2H, o-Py), 7.72 (t, 1H, p-Py), 7.24 (t, 2H, m-Py), 5.32 (s, 2H, CH), 3.16 (s, 3H, Ir—OCH$_3$), 1.94 (s, 12H, CH$_3$). $^{13}$C{$^1$H} NMR (CDCl$_3$): δ 185.2 (C-acac, C=O), 152.1 (o-Py), 137.5 (p-Py), 124.9 (m-Py), 102.8 (O-acac, CH), 57.9 (OCH$_3$), 26.9 (O-acac, CH$_3$). HRMS (MALDI-TOF): Calculated for C$_{16}$H$_{22}$IrNO$_5$Na (M+Na) 524.1025. found 524.1043.

CH activation reaction between 2 and benzene according to FIG. 4: To a re-sealable Schlenk tube was added 2 (5 mg, 0.011 mmol), and benzene (1 mL). The resulting suspension was thoroughly degassed before being placed under an atmosphere of argon. The tube was sealed and then heated to 160° C. in an oil bath for 10 min. After a few minutes of heating, the solid dissolved to yield a clear orange-yellow solution that lightened over the course of the reaction to clear light yellow. After cooling to room temperature, the solvent was removed to yield a yellow solid which was characterized as the iridium phenyl complex which has been previously reported by our group.[4a] $^1$H NMR (THF-d8): δ 6.65 (m, 3H, Ph), 6.57 (m, 2H, Ph), 5.21 (s, 2H, CH), 1.77 (s, 12H, CH$_3$), $^{13}$C{1H} NMR (THF-d$_8$): δ 184.5 (s, O-acac, C=O), 136.3 (s, Ph), 125.3 (s, Ph), 122.9 (s, Ph), 103.0 (s, O-acac, CH), 26.6 (s, O-acac, CH$_3$). Further treatment of this material with pyridine yielded the pyridyl derivative, which had been previously reported. $^1$H NMR (CDCl$_3$): δ 8.52 (m, 2H, py), 7.81 (m, 1H, py), 7.46 (m, 2H, py), 6.99 (m, 5H, Ph), 5.14 (s, 2H, CH), 1.80 (s, 12H, CH$_3$), $^{13}$C{1H} NMR (THF-d$_8$): δ 184.5 (s, O-acac, C=O), 149.7 (s, py), 137.3 (s, Ph), 135.7 (s, py), 131.3 (s, Ph), 125.2 (s, py), 124.5 (s, Ph), 103.2 (s, O-acac, CH), 27.2 (s, O-acac, CH$_3$). MS (ESI): Calculated for C$_{21}$H$_{25}$IrNO$_4$ (M+H) 548.14. found 548.20.

CH activation experiment with 2-$^{13}$C: To prepare the $^{13}$C labeled complex, a 5 mL screw-cap vial was charged with 2-CH$_3$OH (10 mg, 0.022 mmol) and $^{13}$CH$_3$OH (0.5 mL). The vial was then sealed, and placed in an inert atmosphere (Ar) glovebox for 4 days. The resulting yellow-orange solution was then was evaporated under vacuum, yielding a yellow-orange solid. The solid was then transferred to a Schlenk tube, 5 mL of pyridine was added, and the tube was placed in an oil bath regulated at 55° C. for 30 min. A yellow-orange solid was obtained after the volatiles were removed under vacuum. The complex was estimated to be 62% $^{13}$C enriched by comparison of the integration of the doublet resulting from the $^{13}$C-labeled of methoxide protons to that of the singlet of the remaining unlabeled methoxide. $^1$H NMR (C$_6$D$_6$): δ 8.43 (d, 2H, o-Py), 6.58 (t, 1H, p-Py), 6.29 (t, 2H, m-Py), 5.08 (s, 2H, CH), 3.76 (d, 3H, Ir—OCH$_3$, J=140 Hz), 1.67 (s, 12H, CH$_3$). $^{13}$C{$^1$H} NMR (C$_6$D$_6$): δ 185.4 (C-acac, C=O), 102.7 (O-acac, CH), 57.1 (OCH$_3$), 27.3 (O-acac, CH$_3$).

To examine the possibility of the reversible generation of a reactive Ir—H via β-hydride elimination, 2-$^{13}$C (10 mg) was heated in C$_6$D$_6$ (1.5 mL) at 180° C. for 4 h and the $^{13}$C NMR of the crude reaction mixture was obtained. Only $^{13}$CH$_3$OD was detected as was apparent from the clean singlet resonance for the methyl group. To account for the stoichiometric formation of CH$_3$OH, the Ir—H pathway would be expected to lead to generation of the D$^{13}$CH$_2$OD isotopomer (mechanism shown below) whereas the proposed σ-bond metathesis would lead to $^{13}$CH$_3$OH(D).

H-D exchange: Catalytic H-D exchange reactions like those depicted schematically in FIG. 5 were quantified by monitoring the increase of deuterium into C$_6$H$_6$ (R—H and R-D) by GC/MS analyses. This was achieved by deconvoluting the mass fragmentation pattern obtained from the MS analysis, using a program developed with Microsoft EXCEL. An important assumption made with this method is that there are no isotope effects on the fragmentation pattern for the various benzene isotopomers. Fortunately, because the parent ion of benzene is relatively stable towards fragmentation, it can be used reliably to quantify the exchange reactions. The mass range from 78 to 84 (for benzene) was examined for each reaction and compared to a control reaction where no metal catalyst was added. The program was calibrated with known mixtures of benzene isotopomers. The results obtained by this method are reliable to within 5%. Thus, analysis of a mixture of $C_6H_6$, $C_6D_6$ and $C_6H_5D_1$ prepared in a molar ratio of 40:50:10 resulted in a calculated ratio of 41.2($C_6H_6$):47.5($C_6D_6$): 9.9($C_6H_5D_1$). Catalytic H/D exchange reactions were thus run for sufficient reaction times to be able to detect changes >5% exchange. 2 was the catalyst used to carry out the H/D exchange between benzene and deuterium oxide.

In a typical experiment, a 5 mL Schlenk tube was charged with 10 mg of 2-$CH_3OH$, benzene 1 mL, and 0.2 mL of deuterium oxide under an atmosphere of argon. The tube was then placed in a temperature controlled oil-bath maintained at 160° C., and the H/D exchange was measured as described above.

Example 2

H/D Exchange Between $H_2$ and KOD Catalyzed by $Os(acac)_2Cl_2$

Experimental procedure: Two 4 mL glass-lined stainless steel reactors has were set side-to-side, the first one containing 10% wt. solution of KOD in $D_2O$ (approx. 3 M molarity), and the second one containing 10% wt. solution of KOD in $D_2O$ and 5 mg of trans-$Os(acac)_2Cl_2$ (so that the resulting concentration of a complex was approx. 10 mM The reactors were fitted with magnetic stirbars, sealed, purged with argon and pressurized with hydrogen gas to 150 psig each. The reactors were placed into a pre-heated heating block and were heated at 100° C. with stirring for 1 hour. After that the reactors were removed from heating, rapidly cooled in an ice bath, and the gas phases were analyzed for hydrogen isotopomers on Hiden HPR-20 mass-spectrometer. Mass-spectra were obtained and were deconvoluted using custom deconvolution table to obtain the ratios of $H_2$, HD, and $D_2$ isotopomers. The experiment containing trans-$Os(acac)_2Cl_2$ complex showed a 15% increase in $D_2$ with KOD over the background level.

Example 3

Oxidation of MTO Using Various Oxidants

Various solutions MTO and various oxidant candidates were prepared and the course of methanol formation followed and determined by $^1H$ NMR. In a typical example, methyl trioxorhenium MTO (16 mg, 0.067 mmol) in 0.8 ml deuterated water ($D_2O$) was added to a 5 mm NMR tube. To this, two equivalents of oxidant were added. Reaction progress was followed by $^1H$ NMR. All reactions were carried out under air. All reactions (except Pyridine-N-oxide) was carried out at room temperature.

The NMR tube was allowed to stand at room temperature for about 1-1.5 hour. Then reaction was monitored to see the appearance of methanol and/or disappearance of MTO. Externally 5 μL $CH_3OH$ was added to confirm Methanol formation (in cases observed) Results are gathered in Table 1

TABLE 1

| | Equiv. | Oxidant | % Methanol | % completion |
|---|---|---|---|---|
| A | 2 | H2O2 | 84% | 86% |
| B | 2 | (CH3)3SiOOSi(CH3)3 | 90% | 100% |
| C | 4 | PhIO | 85% | 98% |
| D | 2 | mCPBA | 90% | 95% |
| E | 2 | NaIO4 | 95% | 100% |
| F | 2 | Oxone(KHSO5) | 95% | 100% |
| G | 2 | KMnO4 | 32% | 100% |
| H | 2 | KIO3/KOD | 31% | 100% |
| I | 2 | OsO4/2eqKOD | 28% | 78% |
| J | 2 | (CH3)3NO | Not determined | 85% |
| K | 2 | Pyridine N-oxide(60C) | Not determined | 100% |

% completion is percentage of the MTO left relative to the amount of MTO before the oxidant was added.
Amount of Intial MTO present was calibrated with respect to external standard(cyclohexane). 100% completion means all the MTO has reacted.
Varian Mercury 400 (400.151 MHz for $^1H$) spectrometer. Chemical shifts are given in ppm relative to residual solvent proton. Resonances ($D_2O$ at 4.79 ppm). Cyclohexane (5 microL in 2 ml $CCl_4$) was used as an external standard.

We claim:

1. A process for selective oxidation of hydrocarbons, wherein selectivity is of an unreacted hydrocarbon and not an oxidized hydrocarbon, comprising
    passing a feed comprising hydrocarbons and an oxidant to a first catalyst zone comprising an activated metal catalyst, at functionalization conditions, to form an effluent comprising selectively oxidized hydrocarbon product and reduced oxidant;
    separating the selectively oxidized hydrocarbon product from the reduced oxidant;
    passing the reduced oxidant and a reoxidizer to a reoxidation zone, at reoxidizing conditions, to reform the oxidant;
wherein the activated metal catalyst comprises a transition metal selected from the group consisting of Re, Os, Ir, Ru, W, and Rh, where the metal is coordinated to one or more oxidation resistant ligands, and wherein the functionalization conditions comprise a temperature of between 100 and 350 degrees C. and a solvent having an acidity level selected from the group consisting of neutral, basic, and highly basic, thereby producing a selectively oxidized hydrocarbon product.

2. The process of claim 1 wherein the feed comprises an alkane and the selectively oxidized hydrocarbon product comprises an alcohol.

3. The process of claim 2 wherein the feed comprises methane and the product selectively oxidized hydrocarbon comprises methanol.

4. The process of claim 1, wherein said one or more oxidation resistant ligand is selected from the group consisting of hydroxy, alkoxy, oxo, carboxylate, optionally substituted diol, optionally substituted catechol, optionally substituted polyol, and optionally substituted acetylacetonate.

5. The process of claim 1, wherein said one or more oxidation resistant ligand is selected from the group consisting of ammine, optionally substituted amine, optionally substituted amide, optionally substituted nitrogen heterocycle, optionally substituted chelating diamine, optionally substituted chelating polyamine, optionally substituted chelating amide, and optionally substituted linked nitrogen heterocycle.

6. The process of claim 1 wherein the first catalyst zone further comprises a solvent selected from the group consisting of amine and conjugate base amides, alcohol and conjugate base alkoxide, water-containing hydroxides, and a molten salt mixture.

7. The process of claim 1 wherein the functionalization conditions comprise a temperature of between 150 and 250 degrees C.

8. The process of claim 1 wherein the reoxidizer is oxygen.

9. The process of claim 1 wherein the reoxidizer is air.

10. The process of claim 1 wherein the activated metal catalyst is supported on a solid support.

11. The process of claim 1 wherein the oxidant is an O-atom donor.

12. The process of claim 11 wherein the O-atom donor is selected from the group consisting of cupric oxide (CuO), selenate, ($SeO_4^{2-}$), vanadate ($VO_4^{3-}$), and sulfoxide.

13. The process of claim 1, wherein the solvent is neutral.

14. The process of claim 1, wherein the solvent is basic.

15. The process of claim 1, wherein the solvent is highly basic.

16. The process of claim 1, wherein the solvent is selected from the group consisting of amine and conjugate base amides, alcohol and conjugate base alkoxide, water-containing hydroxides, and a molten salt mixture.

17. The process of claim 1, wherein the feed comprises an arene.

18. The process of claim 17, wherein the arene is benzene.

19. The process of claim 1, wherein the process does not operate by the generation of free radicals.

* * * * *